United States Patent [19]

Barner et al.

[11] Patent Number: 5,430,194

[45] Date of Patent: Jul. 4, 1995

[54] PROCESS FOR IMPROVING ENANTIOMERIC PURITY OF ALDEHYDES

[75] Inventors: Bruce A. Barner, Scott Depot; John R. Briggs, Charleston; Jonathan J. Kurland, Charleston; Charles G. Moyers, Jr., Charleston, all of W. Va.

[73] Assignee: Union Carbide Chemicals & Plastics Technology Corporation, Danbury, Conn.

[21] Appl. No.: 265,207

[22] Filed: Jun. 24, 1994

[51] Int. Cl.[6] .................. C07C 45/50; C07C 45/67; C07C 45/78
[52] U.S. Cl. .................. 568/429; 568/426; 568/427; 568/433; 568/438; 568/454
[58] Field of Search .............. 568/426, 427, 454, 429, 568/433, 438

[56] References Cited

U.S. PATENT DOCUMENTS

| | | | |
|---|---|---|---|
| 4,242,193 | 12/1980 | Moeglch | 204/296 |
| 5,248,813 | 9/1993 | Manimaran et al. | 562/401 |
| 5,260,482 | 11/1993 | Pringle et al. | 562/401 |

FOREIGN PATENT DOCUMENTS

| | | | |
|---|---|---|---|
| 275623 | 1/1990 | Germany | B01J 31/18 |
| 280473 | 7/1990 | Germany | B01J 31/18 |
| 8608835 | 11/1988 | WIPO | C07C 333/22 |
| 9303839 | 3/1993 | WIPO | B01J 31/24 |

OTHER PUBLICATIONS

Wink, Donald J. et al., Inorg. Chem. 1990, 29, 5006–5008.
Stille, John K. et al., Organometallics 1991, 10, 1183–1189.
Pottier, Y. et al., Journal of Organometallic Chemistry, 370 (1989), 333–342.
Manimaran et al., Tetrahedron: Asymmetry vol. 4, No. 8, pp. 1949–1954, 1993.
RajanBabu et al., J. Am. Chem. Soc. 1992, 114, 6265–6266.

*Primary Examiner*—Werren B. Lone
*Attorney, Agent, or Firm*—Eugene C. Trautlein

[57] ABSTRACT

The present invention relates to a process for producing an optically active aldehyde (first aldehyde) containing a reduced amount of the corresponding enantiomeric aldehyde (second aldehyde) which process comprises: (1) providing an initial solution containing a non-eutectic mixture of the first aldehyde and the second aldehyde, which mixture has a composition in the compositional region where only the first aldehyde crystallizes when its solubility limit in the solution is exceeded, and (2) maintaining the solution at a temperature above the eutectic temperature of the mixture and under conditions such that the solubility limit of the first aldehyde is exceeded so as to form a crystalline first aldehyde containing relatively less of the second aldehyde than was present in the initial solution.

15 Claims, 11 Drawing Sheets

PROCESS FOR IMPROVING ENANTIOMERIC PURITY OF ALDEHYDES

BACKGROUND OF THE INVENTION

1. Field of the Invention

The present invention relates to a process for improving the enantiometric purity of mixtures of optically active aldehyde isomers.

2. Description of Related Art

Asymmetric synthesis is of importance, for example, in the pharmaceutical industry, since frequently only one optically active isomer (enantiomer) is therapeutically active. An example of such a pharmaceutical product is the non-steroidal anti-imflammatory drug naproxen. The S enantiomer is a potent anti-arthritic agent while the R enantiomer is a liver toxin. It is therefore oftentimes desirable to selectively produce one particular enantiomer over its mirror image.

It is known that special precautions must be taken to ensure production of a desired enantiomer because of the tendency to produce optically inactive racemic mixtures, that is equal amounts of each mirror image enantiomer whose opposite optical activities cancel out each other. In order to obtain the desired enantiomer (or mirror image stereoisomer) from such a racemic mixture, the racemic mixture must be separated into its optically active components. This separation, known as optical resolution, may be carried out by actual physical sorting, direct crystallization of the racemic mixture, or other methods known in the art (see, for example, U.S. Pat. No. 4,242,193). Such optical resolution procedures are often laborious and expensive as well as destructive to the desired enantiomer. Due to these difficulties, increased attention has been placed upon asymmetric synthesis in which one of the enantiomers is obtained in significantly greater amounts than the other enantiomer. Efficient asymmetric synthesis desirably affords the ability to control both regioselectivity (branched/normal isomer ratio) and stereoselectivity.

Various asymmetric synthesis catalysts have been described in the art. For example, Wink, Donald J. et al., Inorg. Chem. 1990, 29, 5006–5008 discloses the synthesis of chelating bis(dioxaphospholane) ligands through chlorodioxaphospholane intermediates and the utility of bis(phosphite)rhodium cations in hydrogenation catalysis. A complex derived from dihydrobenzoin was tested as a precursor in the hydroformylation of olefins and gave a racemic mixture. Cationic rhodium complexes of bis(dioxaphospholane) ligands were tested in the hydrogenation of enamides and gave enantiomeric excesses on the order of 2–10%.

Pottier, Y. et al., Journal of Organometallic Chemistry, 370, 1989, 333–342 describes the asymmetric hydroformylation of styrene using rhodium catalysts modified with aminophosphinephosphinite ligands. Enantioselectivities greater than 30% ee are reportedly obtained.

East Germany Patents Nos. 275,623 and 280,473 relate to chiral rhodium carbohydrate-phosphinite catalyst production. The catalysts are stated to be useful as stereospecific catalysts for carrying out carbon-carbon bond formation, hydroformylation, hydrosilylation, carbonylation and hydrogenation reactions to give optically active compounds.

Stille et al., Organometallics 1991, 10, 1183–1189 relates to the synthesis of three complexes of platinum II-containing the chiral ligands: 1-(tert-butoxycarbonyl)-(2S, 4S)-2-[(diphenylphosphino)methyl]-4-(dibenzophospholyl)pyrrolidine; 1-(tertbutoxycarbonyl)-(2S,4S)-2-[(dibenzophos-pholyl)methyl]-4-(diphenylphosphino)pyrrolidine; and 1-(tert-butoxycarbonyl)-(2S,4S)-4-(dibenzophospholyl)-2 -[(dibenzophospholyl)methyl]pyrrolidine. Asymmetric hydroformylation of vinyl arenes (including methoxyvinylnaphthalene) was examined with use of platinum complexes of these three ligands in the presence of stannous chloride as catalyst. Various branched/normal ratios (0.5–3.2) and enantiomeric excess values (12–77%) were obtained. When the reactions were carried out in the presence of triethyl orthoformate to improve on the enantiomeric purity of the products, all four catalysts gave virtually complete enantioselectivity (ee>96%) and similar branched/normal ratios. A similar disclosure appears in published PCT patent application WO 88/08835

Published Patent Cooperation Treaty Patent Application 93/03839 (Babin et al.) relates to asymmetric syntheses processes in which a prochiral or chiral compound is reacted in the presence of an optically active metal-ligand complex catalyst to produce an optically active product. The processes of Babin et al. are distinctive in that they provide good yields of optically active products having high stereoselectivity, high regioselectivity, and good reaction rate without the need for optical resolution. The processes of Babin et al. stereoselectively produce a chiral center. An advantage of the processes of Babin et al. is that optically active products can be synthesized from optically inactive reactants. Another advantage of the processes of Babin et al. is that yield losses associated with the production of an undesired enantiomer can be substantially reduced. The asymmetric syntheses processes of Babin et al. are useful for the production of numerous optically active organic compounds, e.g., aldehydes, alcohols, ethers, esters, amines, amides, carboxylic acids and the like, which have a wide variety of applications. Despite the remarkable advance in the art represented by Babin et al, there remains further room for improvement with respect to the enantiomeric purity of the optically active aldehyde isomers produced by the Babin et al. processes.

Enantiomeric purification of enantiomerically enriched compounds (e.g., by crystallization) is a well known process and has been observed for many compounds. However, the ability to purify a chiral product via crystallization varies widely from compound to compound and even closely related compounds may behave very differently. There appears to be no prior art relating to the enantiomeric purification of enantiomerically enriched aldehyde mixtures, particularly mixtures of R- and S-2-(6-methoxy-2-naphthyl)propionaldehyde, by crystallization. The following publications are illustrative of prior art related to the crystallization of S-ibuprofen and S-naproxen acids, their sodium salts and 2-(6-methoxy-2-naphthyl)propionitrile from enantiomeric mixtures thereof. These references do not disclose crystallization of enantiomeric aldehyde mixtures.

Manimaran, T.; Stahly, G. P. Tetrahedron: Asymmetry 1993, 4, 1949, "Optical Purification of Profen Drugs," discloses the crystallization of the sodium salts of S-ibuprofen and S-naproxen. Crystallization of the sodium salts results in significant improvement in the enantiomeric purity of the product. The article includes phase diagrams for S-ibuprofen and S-naproxen acids and several salts of each. The article also describes some fundamental principles governing the enantiomeric purification of products via crystallization.

Manimaran, T.; Stahly, G. P.; Herndon, C. R., Jr. U.S. Pat. No. 5,248,813, 1993, "Enantiomeric Resolution," discloses the crystallization of various Ibuprofen salts as a means of improving enantiomeric purity.

Pringle, P.; Murray, W. T.; Thompson, D. K.; Choudhury, A. A.; Patil, D. R. U.S. Pat. No. 5,260,482, 1993, "Enantiomeric Resolution," discloses the use of hydrates of the sodium salt of ibuprofen in crystallization processes which result in enantiomeric purification of the product.

Rajanbabu, T. V.; Casalnuovo, A. L. J. Am. Chem. Soc. 1992, 114, 6265, "Tailored Ligands for Asymmetric Catalysis: The Hydrocyanation of Vinylarenes," discloses the preparation and use of catalysts for the hydrocyanation of vinylarenes as a route for the preparation of S-ibuprofen and S-naproxen. The authors comment, although no experimental details are given, that enantiomerically enriched mixtures of 2-(6-methoxy-2-naphthyl)propionitrile may be purified by crystallization.

The prior art relating to enantiomeric aldehyde mixtures does not disclose the use of crystallization to separate the enantiomers from each other. Thus, in the Stille et al. article discussed above, there is no mention of crystallizing aldehyde mixtures to improve their enantiomeric purity. Babin et al. discussed above discloses: "The desired optically active products, e.g., aldehydes, may be recovered in any conventional manner. Suitable separation techniques include, for example, solvent extraction, crystallization, distillation, vaporization, wiped film evaporation, falling film evaporation and the like. It may be desired to remove the optically active products from the reaction system as they are formed through the use of trapping agents as described in WO Patent 88/08835." Babin et al. does not disclose the use of crystallization to separate enantiomeric aldehydes from each other.

SUMMARY OF THE INVENTION

Figure 1:
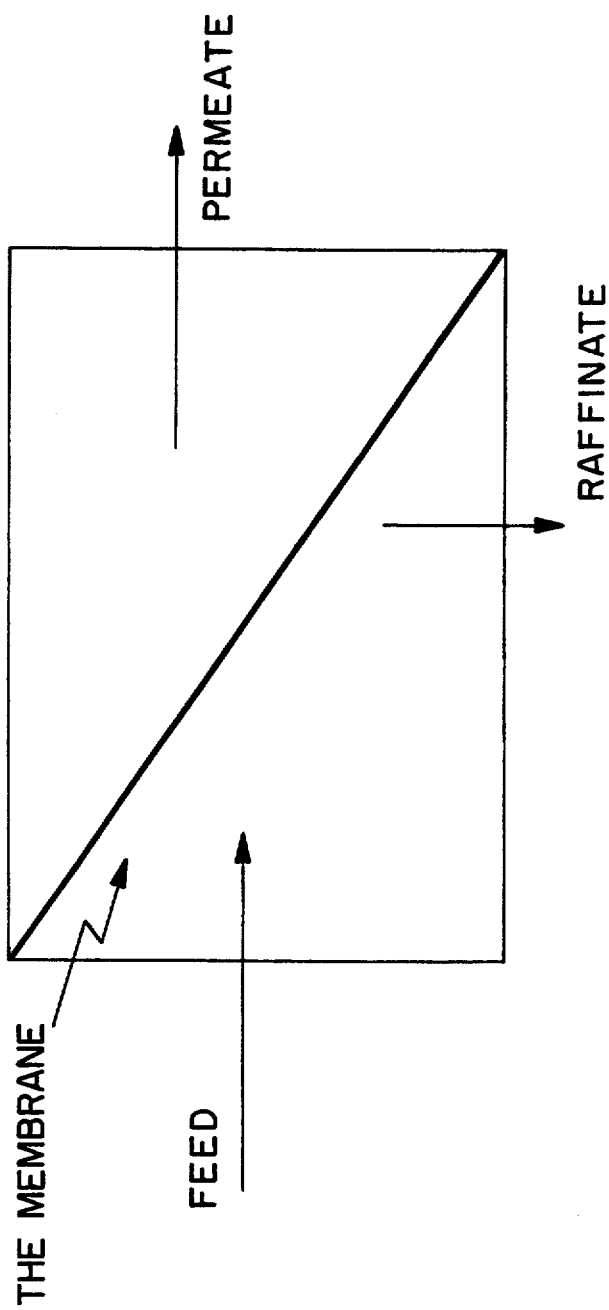
FIG. 1 is a flow diagram illustrating a membrane separation system that can be employed in the practice of the present invention.

This invention provides a process for producing an optically active aldehyde (first aldehyde) containing a reduced amount of the corresponding enantiomeric aldehyde (second aldehyde) which process comprises: (1) providing an initial solution containing a non-eutectic mixture of the first aldehyde and the second aldehyde, which mixture has a composition in the compositional region where only the first aldehyde crystallizes when its solubility limit in the solution is exceeded, and (2) maintaining the solution at a temperature above the eutectic temperature of the mixture and under conditions such that the solubility limit of the first aldehyde in the solution is exceeded so as to form a crystalline first aldehyde containing relatively less of the second aldehyde than was present in the initial solution.

Forming Aldehyde Mixture

The subject invention encompasses first providing a suitable enantiomeric aldehyde mixture. Such mixtures can be provided by such known processes as non-asymmetric processes (e.g., non-asymmetric hydroformylation, non-asymmetric olefin isomerization or non-asymmetric aldol condensation) followed by conventional resolution processes (e.g., chiral chromatography, kinetic resolution or other known resolution methods). However, the enantiomeric aldehyde mixtures are preferably provided by carrying out any known conventional non-asymmetric syntheses of aldehyde mixtures in an asymmetric fashion. In such preferred processes, the catalyst of a conventional non-asymmetric synthesis is replaced by an optically active metal-ligand complex catalyst and the process is conducted to produce a suitable optically active aldehyde mixture. Illustrative such asymmetric syntheses processes include, for example, asymmetric hydroformylation, asymmetric olefin isomerization and asymmetric aldol condensation.

Preferably, the first step of the process of the present invention comprises forming an enantiomeric aldehyde mixture by asymmetric hydroformylation. Such asymmetric hydroformylation processes involve the use of an optically active metal-phosphorus ligand complex catalyst and, optionally, free ligand to produce optically active aldehydes by reacting a prochiral or chiral olefinic compound with carbon monoxide and hydrogen. The optically active aldehydes produced in this preferred first step of the process of the present invention are compounds obtained by the addition of a formyl group to an olefinically unsaturated carbon atom in the starting material with simultaneous saturation of the olefinic bond. The processing techniques of this preferred first step of the process of the present invention may correspond to any of the known processing techniques heretofore employed in conventional asymmetric syntheses reactions, including asymmetric hydroformylation reactions. For instance, the asymmetric syntheses processes can be conducted in continuous, semi-continuous or batch fashion and can involve a liquid recycle operation if desired. This step of processes of this invention are preferably conducted in batch fashion. Likewise, the manner or order of addition of the reaction ingredients, catalyst and solvent are also not critical and may be accomplished in any conventional fashion.

Alternatively, as the first step in the process of the present invention, asymmetric olefin isomerization can be carried out in accordance with conventional procedures known in the art to produce the enantiomeric aldehyde mixtures used in the present invention. For example, allylic alcohols can be isomerized under isomerization conditions in the presence of an optically active metal-ligand complex catalyst described herein to produce optically active aldehydes.

Also alternatively, as the first step in the process of the present invention, asymmetric aldol condensation can be carried out in accordance with conventional procedures known in the art to produce the enantiomeric aldehyde mixtures used in the present invention. For example, optically active aldehydes can be prepared by reacting a prochiral aldehyde and a silyl enol ether under aldol condensation conditions in the presence of an optically active metal-ligand complex catalyst described herein.

In general, the above-mentioned asymmetric synthesis processes are carried out in a liquid reaction medium that contains a solvent for the optically active catalyst, preferably one in which the reaction ingredients including catalyst are substantially soluble. In addition, it may be desired that the asymmetric syntheses processes be effected in the presence of free ligand as well as in the presence of the optically active complex catalyst. By "free ligand" is meant ligand that is not complexed with the metal atom in the optically active complex catalyst.

The prochiral and chiral starting materials useful in the processes for producing the enantiomeric aldehyde mixtures employed in the process of the present this invention are chosen depending on the particular asymmetric synthesis process that is used. Such starting materials are well known in the art and can be used in conventional amounts in accordance with conventional methods. Illustrative starting material reactants include, for example, substituted and unsubstituted aldehydes (for aldol condensation processes), prochiral olefins (for hydroformylation processes) and ketones (for aldol condensation processes) and the like.

Illustrative olefin starting material reactants useful in certain of the asymmetric synthesis processes useful in producing the enantiomeric aldehyde mixtures employed in this invention (e.g., asymmetric hydroformylation) include those which can be terminally or internally unsaturated and be of straight chain, branched-chain or cyclic structure. Such olefins can contain from 2 to 40 carbon atoms or greater and may contain one or more ethylenic unsaturated groups. Moreover, such olefins may contain groups or substituents which do not essentially adversely interfere with the asymmetric syntheses process such as carbonyl, carbonyloxy, oxy, hydroxy, oxycarbonyl, halogen, alkoxy, aryl, haloalkyl, and the like. Illustrative olefinic unsaturated compounds include substituted and unsubstituted alpha olefins, internal olefins, alkyl alkenoates, alkenyl alkanoates, alkenyl alkyl ethers, alkenols and the like, e.g., 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, allyl ethyl ether, n-propyl-7-octenoate, 3-butenenitrile, 5-hexenamide, styrene, norbornene, alpha-methylstyrene and the like. Illustrative preferred olefinic unsaturated compounds include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether, vinyl chloride and the like. Suitable olefinic unsaturated compounds useful in certain asymmetric syntheses processes of this invention include substituted aryl ethylenes described in U.S. Pat. No. 4,329,507, the disclosure of which is incorporated herein by reference. Mixtures of different olefinic starting materials can be employed, if desired, in the asymmetric syntheses processes used as the first step in the process of the subject invention. More preferably, the first step involves hydroformylating alpha olefins containing from 4 to 40 carbon atoms or greater and internal olefins containing from 4 to 40 carbon atoms or greater or mixtures of such alpha olefins and internal olefins.

Illustrative prochiral and chiral olefins useful in the processes that can be employed to produce the enantiomeric aldehyde mixtures that can be employed in this invention include those represented by the formula:

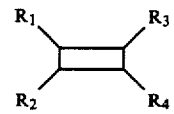

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R-groups are connected to form ring compounds, e.g., 3-methyl-1-cyclohexene, and the like.

The optically active catalyst useful in producing the aldehyde mixtures that are employed in this invention includes an optically active metal-ligand complex catalyst in which the ligand is optically active, preferably optically pure. The permissible metals which make up the optically active metal-ligand complexes include Group VIII metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium and ruthenium, especially rhodium. Other permissible metals include Group IB metals selected from copper (Cu), silver (Ag), gold (Au) and mixtures thereof, and also Group VIB metals selected from chromium (Cr), molybdenum (Mo), tungsten (W) and mixtures thereof. Mixtures of metals from Group VIII, Group IB and Group VIB may be used in this invention. It is to be noted that the successful practice of this invention does not depend and is not predicated on the exact structure of the optically active metal-ligand complex species, which may be present in their mononuclear, dinuclear and or higher nuclearity forms, provided the ligand is optically active. Indeed, the exact optically active structure is not known. Although it is not intended herein to be bound to any theory or mechanistic discourse, it appears that the optically active catalytic species may in its simplest form consist essentially of the metal in complex combination with the optically active ligand and, in hydroformylation, carbon monoxide, hydrogen and an olefin.

The term "complex" as used herein and in the claims means a coordination compound formed by the union of one or more electronically rich molecules or atoms capable of independent existence with one or more electronically poor molecules or atoms, each of which is also capable of independent existence. For example, the preferred optically active ligands employable herein, i.e., phosphorus ligands, may possess one or more phosphorus donor atoms, each having one available or unshared pair of electrons which are each capable of forming a coordinate covalent bond independently or possibly in concert (e.g., via chelation) with the metal. As can be surmised from the above discussions, carbon monoxide (which is also properly classified as ligand) can also be present and complexed with the metal. The ultimate composition of the optically active complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $R_2PO$ and $RP(O)(OH)O$ (wherein each R is alkyl or aryl), acetate, acetylacetonate, $SO_4$, $PF_4$, $PF_6$, $NO_2$, $NO_3$, $CH_3O$, $CH_2=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the optically active complex species is preferably free of any additional organic ligand or anion that might poison the catalyst and have an undue adverse effect on catalyst performance. It is preferred in the rhodium-catalyzed asymmetric hydroformylation reactions of this invention that the active catalysts be free of halogen and sulfur directly bonded to the rhodium, although such may not be absolutely necessary.

The number of available coordination sites on such metals is well known in the art. Thus the optically active species may comprise a complex catalyst mixture, in their monomeric, dimeric or higher nuclearity forms, which are preferably characterized by at least one phosphorus-containing molecule complexed per one molecule of rhodium. As noted above, it is considered that the optically active species of the preferred rhodium catalyst employed in this invention during asymmetric hydroformylation may be complexed with carbon monoxide and hydrogen in addition to the optically active phosphorus ligands in view of the carbon monoxide and hydrogen gas employed by the asymmetric hydroformylation process.

Moreover, regardless of whether the optically active complex catalyst is formed prior to introduction into the reaction zone or whether the active catalyst is prepared in situ during the reaction, the asymmetric synthesis processes (and especially the asymmetric hydroformylation processes) may, if desired, be effected in the presence of free ligand.

The ligands employable in producing the enantiomeric aldehyde mixtures useful in this invention include those optically active ligands having the general formula:

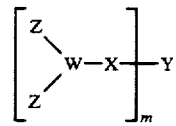

wherein each W is the same or different and is phosphorus, arsenic or antimony, each X is the same or different and is oxygen, nitrogen or a covalent bond linking W and Y, Y is an m-valent substituted or unsubstituted hydrocarbon residue, each Z is the same or different and is a substituted or unsubstituted hydrocarbon residue, preferably a hydrocarbon residue containing at least one heteroatom which is bonded to W, or the Z substituents bonded to W may be bridged together to form a substituted or unsubstituted cyclic hydrocarbon residue, preferably a cyclic hydrocarbon residue containing at least 2 heteroatoms which are each bonded to W, and m is a value equal to the free valence of Y, preferably a value of from 1 to 6, provided at least one of Y and Z is optically active.

Referring to the above general formula, it is appreciated that when m is a value of 2 or greater, the ligand may include any combination of permissible cyclic hydrocarbon residues and/or acyclic hydrocarbon residues which satisfy the valence of Y. It is also appreciated that the hydrocarbon residues represented by Z may include one or more heteroatoms and such heteroatom may be directly bonded to W. The optically active ligands included in the above general structure should be easily ascertainable by one skilled in the art.

Illustrative optically active ligands employable in the first step of the processes this invention include those of the formulae:

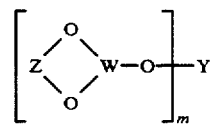

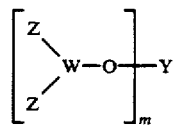

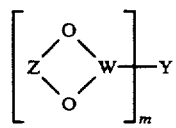

-continued

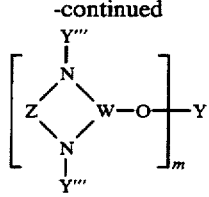

wherein W, Y, Z and m are as defined hereinabove and Y''' is the same or different and is hydrogen or a substituted or unsubstituted hydrocarbon residue. Illustrative preferred optically active ligands encompassed by the above formulae include, for example, (poly)phosphites, (poly)phosphinites, (poly)phosphonites and the like.

Illustrative preferred optically active ligands employable in this invention include the following:

(i) optically active polyphosphites having the formula:

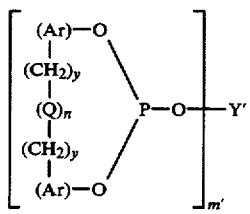

wherein each Ar group is the same or different and is a substituted or unsubstituted aryl radical; Y' is an m-valent substituted or unsubstituted hydrocarbon radical selected from alkylene, alkylene-oxyalkylene, arylene and arylene-($CH_2$)$_y$-(Q)$_n$-($CH_2$)$_y$- arylene; each y is the same or different and is a value of 0 or 1; each n is the same or different and is a value of 0 or 1; each Q is the same or different and is a substituted or unsubstituted divalent bridging group selected from —$CR^1R^2$—, —O—, —S—, —$NR^3$—, —$SiR^4R^5$— and —CO—, wherein $R^1$ and $R^2$ are the same or different and are hydrogen or a substituted or unsubstituted radical selected from alkyl of 1 to 12 carbon atoms, phenyl, tolyl and anisyl, and $R^3$, $R^4$ and $R^5$ are the same or different and are a radical selected from hydrogen or methyl; and m' is a value of from 2 to 6;

(ii) optically active diorganophosphites having the formula:

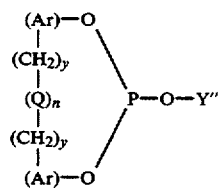

wherein Y'' is a substituted or unsubstituted monovalent hydrocarbon radical, and Ar, Q, n and y are as defined above; and (iii) optically active open-ended bisphosphites having the formula:

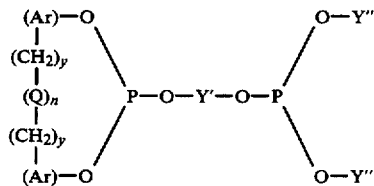

wherein Ar, Q, n, y, Y' and Y'' are as defined above and Y'' can be the same or different.

Illustrative aryl radicals of the Ar and Y' groups of the above formulae include aryl moieties which may contain from 6 to 18 carbon atoms such as phenylene, naphthylene, anthracylene and the like. In the above formulae, preferably m is from 2 to 4 and each y and each n has a value of 0. However, when n is 1, Q preferably is a —$CR^1R^2$—bridging group as defined above and more preferably methylene (—$CH_2$—) or alkylidene (—$CHR_2$—), wherein $R^2$ is an alkyl radical of 1 to 12 carbon atoms (e.g., methyl, ethyl, propyl, isopropyl, butyl, dodecyl, etc.), especially methyl.

The m-valent hydrocarbon radicals represented by Y' in the polyphosphite ligand formula above are hydrocarbons containing from 2 to 30 carbon atoms selected from alkylene, alkylene-oxyalkylene, arylene, and arylene-(—$CH_2$—)$_y$—(Q)$_n$—(—$CH_2$—)$_y$— arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

The divalent bridging group represented by Y' in the open-ended bisphosphite ligand formula above are divalent hydrocarbons containing from 2 to 30 carbon atoms selected from alkylene, alkylene-oxy-alkylene, arylene and arylene-(—$CH_2$—)$_y$—(Q)$_n$— (—$CH_2$—)$_y$—arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

Hydrocarbon radicals represented by Y'' in the above phosphite ligand formulae include monovalent hydrocarbon radicals containing from 1 to 30 carbon atoms selected from alkyl radicals including linear or branched primary, secondary or tertiary alkyl radicals, such as methyl, ethyl, n-propyl, isopropyl, amyl, sec-amyl, t-amyl, 2-ethylhexyl and the like; aryl radicals such as phenyl, naphthyl and the like; aralkyl radicals such as benzyl, phenylethyl, tri-phenylmethylethane and the like; alkaryl radicals such as tolyl, xylyl and the like; and cycloalkyl radicals such as cyclopentyl, cyclohexyl, cyclohexylethyl and the like. Preferably, Y'' is selected from alkyl and aryl radicals which contain from about 1 and 30 carbon atoms. Preferably, the alkyl radicals contain from 1 to 18 carbon atoms, most preferably from 1 to 10 carbon atoms, while the aryl, aralkyl, alkaryl and cycloalkyl radicals preferably contain from 6 to 18 carbon atoms. Further, although each Y'' group in the open-ended bisphosphite ligand formula above may differ from the other, preferably they are identical.

The aryl radicals in the above formulae may also be substituted with any substituent radical that does not unduly adversely affect the processes of this invention. Illustrative substituents include radicals containing from 1 to 18 carbon atoms such as alkyl, aryl, aralkyl, alkaryl and cycloalkyl radicals; alkoxy radicals; silyl radicals such as —Si($R^9$) and —Si(O$R^9$)$_3$; amino radicals such as —N($R^9$)$_2$; acyl radicals such as —C(O)$R^9$; acyloxy radicals such as —OC(O)$R^9$; carbonyloxy radicals such as —COO$R^9$; amido radicals such as —C(O)N($R^9$) and —N($R^9$)CO$R^9$; sulfonyl radicals such as —SO$_2R^9$; sulfinyl radicals such as —SO($R^9$)$_2$; thionyl radicals such as —S$R^9$; phosphonyl radicals such as —P(O)($R^9$)$_2$; as well as halogen, nitro, cyano, trifluoromethyl and hydroxy radicals and the like, wherein each $R^9$ can be a monovalent hydrocarbon radical such as alkyl, aryl, alkaryl, aralkyl and cycloalkyl radicals, with the provisos that in amino substitutents such as —N($R^9$)$_2$, each $R^9$ taken together can also comprise a divalent bridging group that forms a heterocyclic radical with the nitrogen atom, in amido substituents such as —C(O)N($R^9$) and —N($R^9$)CO$R^9$, each $R^9$ bonded to N can also be hydrogen, and in phosphonyl substituents such as —P(O)($R^9$)$_2$, one $R^9$ can be hydrogen. It is to be understood that each $R^9$ group in a particular substituent may be the same of different. Such hydrocarbon substituent radicals could possibly in turn be substituted with a substituent such as already herein outlined above provided that any such occurrence would not unduly adversely effect the processes of this invention. At least one ionic moiety selected from salts of carboxylic acid and of sulfonic acid may be substituted on an aryl moiety in the above formulae.

Among the more preferred phosphite ligands useful in the first step in the process of the present invention are those ligands wherein the two Ar groups linked by the bridging group represented by —(CH$_2$)$_y$—(Q)$_n$—(CH$_2$)$_y$— in the above formulae are bonded through their ortho positions in relation to the oxygen atoms that connect the Ar groups to the phosphorus atom. It is also preferred that any substituent radical, when present on such Ar groups, be bonded in the para and/or ortho position on the aryl in relation to the oxygen atom that bonds the substituted Ar group to its phosphorus atom.

Illustrative monovalent hydrocarbon residues represented by the Z, Y, Y" and Y'" groups in the above formulae include substituted or unsubstituted monovalent hydrocarbon radicals containing from 1 to 30 carbon atoms selected from substituted or unsubstituted alkyl, aryl, alkaryl, aralkyl and alicyclic radicals. While each Z and Y" group in a given formula may be individually the same or different, preferably they are both the same. More specific illustrative monovalent hydrocarbon residues represented by Z, Y, Y" and Y'" include primary, secondary and tertiary chain alkyl radicals such as methyl, ethyl, propyl, isopropyl, butyl, sec-butyl, t-butyl, neo-pentyl, sec-amyl, t-amyl, iso-octyl, 2-ethylhexyl, iso-nonyl, iso-decyl, octadecyl and the like; aryl radicals such as phenyl, naphthyl, anthracyl and the like; aralkyl radicals such as benzyl, phenylethyl and the like; alkaryl radicals such as tolyl, xylyl, p-alkylphenyls and the like; and alicyclic radicals such as cyclopentyl, cyclohexyl, cyclooctyl, cyclohexylethyl, 1-methylcyclohexyl and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms. Among the more preferred Z, Y, Y" and Y'" residues are phenyl and substituted phenyl radicals.

Illustrative divalent hydrocarbon residues represented by Z, Y and Y' in the above formulae include substituted and unsubstituted radicals selected from alkylene, -alkylene-oxyalkylene, arylene, arylene-oxyarylene-, alicyclic radicals, phenylene, naphthylene,-arylene-(CH$_2$)$_y$(Q)$_n$(CH$_2$)$_y$-arylene- such as -phenylene-(CH$_{12}$)$_y$(Q)$_n$(CH$_2$)$_y$—phenylene- and-naphthylene-(CH$_2$)$_y$(Q)$_n$(CH$_2$)$_y$-naphthylene-radicals, wherein Q, y and n are as defined hereinabove. More specific illustrative divalent radicals represented by Z, Y and Y' include, e.g., 1,2-ethylene, 1,3-propylene, 1,6-hexylene, 1,8-octylene, 1,12-dodecylene, 1,4-phenylene, 1,8-naphthylene, 1,1'-biphenyl-2,2'-diyl, 1,1'-binaphthyl-2,2'-diyl, 2,2'-binaphthyl-1,1'-diyl and the like. The alkylene radicals may contain from 2 to 12 carbon atoms, while the arylene radicals may contain from 6 to 18 carbon atoms. Preferably Z is an arylene radical, Y is an alkylene radical and Y' is an alkylene radical.

Moreover, the above-described radicals represented by Z, Y, Ar, Y' and Y" of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radicals as defined above. In addition, various other substituents that may be present include, e.g., halogen, preferably chlorine or fluorine, —NO$_2$, —CN, —CF$_3$, —OH, —Si(CH$_3$)$_3$, —Si(OCH$_3$)$_3$, —Si(C$_3$H$_7$)3, —C(O)CH$_3$, —C(O)C$_2$H$_5$, —OC(O)C$_6$H$_5$, —C(O)OCH$_3$, —N(CH$_3$)2, —NH$_2$, —NHCH$_3$, —NH(C$_2$H$_5$), —CONH$_2$, —CON(CH$_3$)$_2$, —S(O)$_2$C$_2$H$_5$, —OCH$_3$, —OC$_2$H$_5$, —OC$_6$H$_5$, —C(O)C$_6$H$_5$, —O(t—C$_4$H$_9$), —SC$_2$H$_5$, —OCH$_2$CH$_2$OCH$_3$, —(OCH$_2$CH$_2$)$_2$OH$_3$, —(OCH$_2$CH$_2$)$_3$OCH$_3$, —SCH$_3$, —S(O)CH$_3$, —SC$_6$H$_5$, —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_3$)$_2$, —P(O)CH$_3$(C$_6$H$_5$), —P(O)(H)(C$_6$H$_5$), —NHC(O)CH$_3$ and the like. Moreover, each Z, Y, Ar, Y' and Y" group may contain one or more such substituent groups which may also be the same or different in any given ligand molecule. Preferred substituent radicals include alkyl and alkoxy radicals containing from 1 to 18 carbon atoms and more preferably from 1 to 10 carbon atoms, especially t-butyl and methoxy.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The optically active ligands employed in the complex catalysts useful in the first step of the process of this invention are uniquely adaptable and suitable for asymmetric syntheses processes, especially rhodium-catalyzed asymmetric hydroformylation. For instance, the optically active phosphorus ligands may provide very good rhodium complex stability in addition to providing good catalytic activity for the asymmetric hydroformylation of all types of permissible olefins. Further, their unique chemical structure should provide the ligand with very good stability against side reactions such as being hydrolyzed during asymmetric hydroformylation, as well as upon storage.

The types of novel optically active ligands of the generic class employable in the first step of the process of this invention can be prepared by methods known in the art. For instance, the optically active phosphorus ligands employable in this invention can be prepared via a series of conventional phosphorus halide-alcohol or amine condensation reactions in which at least one of the alcohol or amine ingredients is optically active or optically pure. Such types of condensation reactions and the manner in which they may be conducted are well known in the art. Moreover, the phosphorus ligands employable herein can be readily identified and characterized by conventional analytical techniques, such as Phosphorus-31 nuclear magnetic resonance spectroscopy and Fast Atom Bombardment Mass Spectroscopy if desired.

As noted above, the optically active ligands can be employed as both the ligand of the above-described optically active metal-ligand complex catalyst as well as the free ligand that can be present in the reaction medium of the processes of this invention. In addition, while the optically active ligand of the metal-ligand complex catalyst and any excess free ligand preferably present in a given process of this invention are normally the same ligand, different optically active ligands, as well as mixtures of two or more different optically active ligands, may be employed for each purpose in any given process.

The optically active metal-ligand complex catalysts of this invention may be formed by methods known in the art. See, for example, U.S. Pat. Nos. 4,769,498, 4,717,775, 4,774,361, 4,737,588, 4,885,401, 4,748,261, 4,599,206, 4,668,651, 5,059,710 and 5,113,022, all of which are incorporated herein by reference. For instance, preformed metal hydrido-carbonyl catalysts may possibly be prepared and introduced into the reaction medium of an asymmetric syntheses process. More preferably, the metal-ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the ligand for the in situ formation of the active catalyst. In a preferred embodiment, rhodium dicarbonyl acetylacetonate is employed as a rhodium precursor and reacted in the presence of a solvent with a phosphorus ligand compound to form a catalytic rhodium-phosphorus complex precursor which is introduced into the reactor, optionally along with excess free phosphorus ligand, for the in situ formation of the active catalyst. In any event, it is sufficient for the purpose of this invention to understand that an optically active metal-ligand complex catalyst is present in the reaction medium under the conditions of the asymmetric syntheses and more preferably asymmetric hyroformylation process.

Moreover, the amount of optically active complex catalyst present in the reaction medium need only be that minimum amount necessary to provide the given metal concentration desired to be employed and which will furnish the basis for at least that catalytic amount of metal necessary to catalyze the particular asymmetric syntheses process desired. In general, metal concentrations in the range of from about 1 ppm to about 10,000 ppm, calculated as free metal, and ligand to metal mole ratios in the catalyst ranging from about 0.5:1 to about 200:1, should be sufficient for most asymmetric syntheses processes. Moreover, in the rhodium catalyzed asymmetric hydroformylation processes of this invention, it is generally preferred to employ from about 10 to 1000 ppm of rhodium and more preferably from 25 to 750 ppm of rhodium, calculated as free metal.

A further aspect of the first step of the process of this invention involves the use of a catalyst precursor composition consisting essentially of a solubilized metal-ligand complex precursor catalyst, an organic solvent and free ligand. Such precursor compositions may be prepared by forming a solution of a metal starting material, such as a metal oxide, hydride, carbonyl or salt e.g., a nitrate, which may or may not be in complex combination with an optically active ligand, an organic solvent and a free ligand as defined herein. Any suitable metal starting material may be employed, e.g., rhodium dicarbonyl acetylacetonate, $Rh_2O_3$, $Rh_4(CO)_{12}$, $Rh_6(CO)_{16}$, $Rh(NO_3)_3$, poly-phosphite rhodium carbonyl hydrides, iridium carbonyl, poly-phosphite iridium carbonyl hydrides, osmium halide, chlorosmic acid, osmium carbonyls, palladium hydride, palladous halides, platinic acid, platinous halides, ruthenium carbonyls, as well as other salts of other metals and carboxylates of $C_2$–$C_{16}$ acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course, any suitable solvent may be employed such as those employable in the asymmetric syntheses process desired to be carried out. The desired asymmetric syntheses process may of course also dictate the various amounts of metal, solvent and optically active ligand present in the precursor solution. Optically active ligands if not already complexed with the initial metal may be complexed to the metal either prior to or in situ during the asymmetric syntheses process.

The optically active catalyst used in the first step of the process of the present invention may optionally be supported. Advantages of a supported catalyst may include ease of catalyst separation and ligand recovery. Illustrative examples of supports include alumina, silica gel, ion-exchange resins, polymeric supports and the like.

The process conditions employable in the asymmetric processes that can be employed in the first step of the process of this invention are chosen depending on the particular asymmetric synthesis process. Such process conditions are well known in the art. All of the asymmetric syntheses processes useful in this invention can be carried out in accordance with conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference. Depending on the particular process, operating temperatures can range from about −80° C. or less to about 500° C. or greater and operating pressures can range from about 1 psig or less to about 10,000 psig or greater.

The reaction conditions for effecting the preferred asymmetric hydroformylation process that can be employed in the first step of the process of this invention may be those heretofore conventionally used and may comprise a reaction temperature of from about −25° C. or lower to about 200° C. and pressures ranging from about 1 to 10,000 psia. While the preferred asymmetric syntheses process is the hydroformylation of olefinically unsaturated compounds carbon monoxide and hydrogen to produce optically active aldehydes, it is to be understood that the optically active metal-ligand complexes may be employed as catalysts in other types of asymmetric syntheses processes to obtain good results.

As noted, the first step of the preferred process of this invention involves the production of optically active aldehydes via asymmetric hydroformylation of a prochiral or chiral olefinic unsaturated compound with carbon monoxide and hydrogen in the presence of an optically active metal-phosphorus ligand complex catalyst and, optionally, free phosphorus ligand, especially an optically active rhodium-phosphorus ligand complex catalyst.

While the optimization of the reaction conditions necessary to achieve the best results and efficiency desired are dependent upon experience in the utilization of the subject invention, only a certain measure of experimentation should be necessary to ascertain those conditions which are optimum for a given situation and such should be well within the knowledge of one skilled in the art and easily obtainable by following the more preferred aspects of this invention as explained herein and/or be simple routine experimentation. For instance, the total gas pressure of hydrogen, carbon monoxide and olefinic unsaturated starting compound of the preferred asymmetric hydroformylation process of this invention may range from about 1 to about 10,000 psia. More preferably, however, in the asymmetric hydroformylation of prochiral olefins to produce optically active aldehydes, it is preferred that the process be operated at a total gas pressure of hydrogen, carbon monoxide and olefinic unsaturated starting compound of less than about 1500 psia, and more preferably less than about 1000 psia. The minimum total pressure of the reactants is not particularly critical and is limited predominately only by the amount of reactants necessary to obtain a desired rate of reaction. More specifically, the carbon monoxide partial pressure of the asymmetric hydroformylation process of this invention is preferably from about 1 to about 360 psia, and more preferably from about 3 to about 270 psia, while the hydrogen partial pressure is preferably about 15 to about 480 psia and more preferably from about 30 to about 300 psia. In general, the molar ratio of gaseous hydrogen to carbon monoxide may range from about 1:10 to 100:1 or higher, the more preferred hydrogen to carbon monoxide molar ratio being from about 1:1 to about 1:10. Higher molar ratios of carbon monoxide to gaseous hydrogen may generally tend to favor higher branched/normal isomer ratios.

Further as noted above, the preferred asymmetric hydroformylation process useful in the first step of the process of this invention may be conducted at a reaction temperature from about −25° C. or lower to about 200° C. The preferred reaction temperature employed in a given process will of course be dependent upon the particular olefinic starting material and optically active metal-ligand complex catalyst employed as well as the efficiency desired. Lower reaction temperatures may generally tend to favor higher enantiomeric excesses (ee) and branched/normal ratios. In general, asymmetric hydroformylations at reaction temperatures of about 0° C. to about 120° C. are preferred for all types of olefinic starting materials. More preferably, alpha-olefins can be effectively hydroformylated at a temperature of from about 0° C. to about 90° C. while even less reactive olefins than conventional linear alphaolefins and internal olefins as well as mixtures of alpha-olefins and internal olefins are effectively and preferably hydroformylated at a temperature of from about 25° C. to about 120° C. Indeed, in the rhodium-catalyzed asymmetric hydroformylation process of this invention, no substantial benefit is seen in operating at reaction temperatures much above 120° C. and such is considered to be less desirable.

The processes employed in the first step of the process of this invention are conducted for a period of time sufficient to produce an enantiomeric aldehyde mixture. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

The asymmetric synthesis processes, preferably asymmetric hydroformylation processes, useful as the first step in the process of this invention can be carried out in either the liquid or gaseous state and involve a batch, continuous liquid or gas recycle system or combination of such systems. A batch system is preferred for conducting such processes. Preferably, such asymmetric hydroformylation involves a batch homogeneous catalysis process wherein the hydroformylation is carried out in the presence of both free phosphorus ligand and any suitable conventional solvent as further described herein.

The asymmetric synthesis processes, and preferably asymmetric hydroformylation process, useful as the first step in the process of this invention may be conducted in the presence of an organic solvent for the optically active metal-ligand complex catalyst. Depending on the particular catalyst and reactants employed, suitable organic solvents include, for example, alcohols, alkanes, alkenes, alkynes, ethers, aldehydes, ketones, esters, acids, amides, amines, aromatics and the like. Any suitable solvent which does not unduly adversely interfere with the intended asymmetric synthesis process can be employed and such solvents may include those heretofore commonly employed in known metal catalyzed processes. Increasing the dielectric constant or polarity of a solvent may generally tend to favor increased reaction rates and selectivity. Mixtures of one or more different solvents may be employed if desired. The amount of solvent employed is not critical to the subject invention and need only be that amount sufficient to provide the reaction medium with the particular metal, substrate and product concentration desired for a given process. In general, the amount of solvent when employed may range from about 5 percent by weight up to about 95 percent by weight or more based on the total weight of the reaction medium.

As noted above, the metal-ligand-catalyzed asymmetric synthesis processes (and especially the asymmetric hydroformylation process) useful as the first step in the process of this invention can be carried out in the presence of free ligand, i.e., ligand that is not complexed with the metal of the optically active metal-ligand complex catalyst employed. While it is preferred to employ a free ligand that is the same as the ligand of the metal-ligand complex catalyst such ligands need not be the same in a given process, but can be different if desired. While the asymmetric syntheses and preferably asymmetric hydroformylation process may be carried out in any excess amount of free ligand desired, the employment of free ligand may not be absolutely necessary. Accordingly, in general, amounts of ligand of from about 2 to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the asymmetric hydroformylation process, at any time and in any suitable manner, to maintain a predetermined level of free ligand in the reaction medium.

The ability to carry out the processes useful as the first step of the process of this invention in the presence of free ligand can be a beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

As indicated above, the aldehyde-forming processes useful in this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone. The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The aldehyde-forming processes useful as the first step in the process of this invention are useful for preparing mixtures of substituted and unsubstituted optically active aldehydes. The aldehyde-forming processes useful in this invention stereoselectively produce a chiral center. Illustrative optically aldehydes prepared by the processes of this invention include, for example, substituted and unsubstituted aldehydes. Illustrative preferred optically active aldehyde compounds prepared by the asymmetric hydroformylation process of this invention include, for example, S-2-(p-isobutylphenyl)propionaldehyde, S-2-(6-methoxy-2-naphthyl)-propionaldehyde, S-2-(3-benzoylphenyl)propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like. Illustrative of suitable optically active compounds which can be prepared by the processes of this invention (including derivatives of the optically active compounds as described hereinbelow and also prochiral and chiral starting material compounds as described hereinabove) include those permissible compounds which are described in Kirk-Othmer, Encyclopedia of Chemical Technology, Third Edition, 1984, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The aldehyde-forming processes useful as the first step in the process of this invention can provide optically active aldehydes having very high enantioselectivity and regioselectivity. Enantiomeric excesses of preferably greater than 50%, more preferably greater than 75% and most preferably greater than 90% can be obtained by such processes. Branched/normal molar ratios of preferably greater than 5:1, more preferably greater than 10:1 and most preferably greater than 25:1 can be obtained by such processes.

In the process of the present invention, the aldehyde mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation and the like. It may be desired to remove the optically active products from the crude reaction mixture as they are formed through the use of trapping agents as described in published Patent Cooperation Treaty Patent ApplicationWO 88/08835. A preferred method for separating the enantiomeric aldehyde mixtures from the other components of the crude reaction mixtures is by membrane separation. Such membrane separation can be achieved as set out below which for purposes of illustration, relates to the separation of a crude asymmetric hydroformylation reaction mixture.

In membrane separation of a crude hydroformylation reaction product, a hydrophobic solvent-resistant membrane is used which allows the aldehyde mixture, any unreacted olefin and any solvent to pass through while retaining a substantial portion of the optically active metal-phosphorus ligand complex catalyst and any free ligand. A flow diagram of a suitable membrane separation system is shown in FIG. 1. The membrane separation is a pressure-driven process and, typically, the pressure of the feed stream (i.e., the crude reaction product that is being separated) is about 400 to 500 pounds per square inch, although pressures as low as 50 pounds per square inch and as high as 1000 pounds per square inch can be used. The feed stream to the membrane is the crude reaction product comprising an optically active, metal-phosphorus ligand complex catalyst and any free ligand dissolved in the aldehyde mixture, the unreacted olefin and any solvent used in the asymmetric hydroformylation. The "permeate" is the stream which has passed through the membrane, as compared to the feed stream, the permeate is at a greatly reduced pressure. Typically, the permeate is near atmospheric pressure. The permeate contains a greatly reduced amount of optically active metal-phosphorus ligand complex catalyst and any free ligand dissolved in the bulk of the aldehyde, the unreacted olefin and any solvent. The "raffinate" stream (also called the "concentrate" or "non-permeate" stream) is the stream that does not pass through the membrane. The raffinate contains the bulk of the optically active metal-phosphorus ligand complex catalyst and any free ligand dissolved in some aldehyde, unreacted olefin and any solvent. The raffinate stream is typically only slightly lower in pressure than the feed stream. The raffinate stream can be recycled back to the hydroformylation reactor for reuse. The permeate stream can be repressurized if it is desired to remove more of the optically active metal-phosphorus ligand complex catalyst and any free ligand catalyst and sent to another membrane to undergo separation again. Alternatively, the permeate stream can be sent to the next step of the process of the present invention (crystallization) if the levels of catalyst and ligand are acceptably low.

Suitable membranes for the above separations are disclosed in published European Patent Application 0 532,199 A1. Such membranes are a composite membranes which are substantially insoluble in acetonitrile, ethanol, hexane, toluene, N-methylpyrrolidone, dimethylsulfoxide, dimethylformamide, dimethylacetamide, mixtures thereof with each other, and mixtures of any of the foregoing with water. The membranes comprise a substrate layer made from a polymer selected from copolymers and homopolymers of ethylenically unsaturated nitriles, which substrate layer has been subjected to a stepwise treatment sequence comprising the steps of: (1) insolubilizing the polymer by crosslinking; (2) coating with a silicone layer; and (3) crosslinking the silicone layer. These membranes can be composite membrane further characterized by at least one of the following features (a), (b), (c) and (d), namely:

(a) the ethylenically unsaturated nitriles are selected from acrylonitrile and substituted acrylonitriles;

(b) prior to step (2), the crosslinked insolubilize substrate obtained in step (1) has been treated with a pore protector in absence of curing agents and catalysts therefor;

(c) the silicone coating layer comprises at least one member selected from the group consisting of silanol-terminated polydimethylsiloxane, other silanol-terminated polysiloxanes, other hydroxy-terminated polysiloxanes, silicones containing alkyl groups, silicones containing aryl groups, and silicones containing both alkyl and aryl groups;

(d) the composite membrane swells to an extent of no more than about 10% when immersed in said solvents.

The pore protector that may be present in such membranes comprises at least one member selected from the group consisting of silanol-terminated polydimethylsiloxane, other silanol-terminated polysiloxanes, other hydroxy-terminated polysiloxanes, silicones containing alkyl groups, silicones containing aryl groups, and silicones containing both alkyl and aryl groups. The substrate layer may be self-supporting or the substrate layer may be supported on another porous material. The insolubilizing step comprises at least step (i) of the following steps (i) and (ii), namely: (i) treatment with at least one base selected from organic and inorganic bases; (ii) subsequently to step (i), subjection of said substrate to heat-treatment, preferably at a temperature within the range of about 110°–130° C. Either the silicone coating or the pore protector, if present, or both, comprises at least one member selected from the group consisting of silicones containing fluorine-substituted alkyl groups, silicones containing fluorine-substituted aryl groups and silicones containing both alkyl and aryl groups wherein either the alkyl groups or the aryl groups, or both the alkyl and aryl groups, are at least partly fluorine-substituted.

Such membranes are composites having an membrane substrate which is a porous material, such as a microfiltration (MF), ultrafiltration (UF) or Reverse Osmosis (RO) membrane. The substrate can be made from a polymer, particularly a copolymer or a homopolymer of an ethylenically unsaturated nitrile. The substrate is preferably treated with a pore protector (in absence of a curing agent) and then coated with a silicone layer which is then crosslinked. The pore protector (which may be, for example, a hydroxy-terminated polysiloxane) serves the dual purposes of: (1) preventing the pores from collapsing when the support is dried during the curing of the subsequently-applied silicone layer and (2) preventing passage of the subsequently-applied silicone layer deeply into the pores and thus also preventing an undue reduction of the flux of the finished membrane. Treatment with the pore protector may be carried out, for example, by dipping the membrane substrate into a dilute solution of the pore protector in a low-boiling inert solvent, (e.g. a low boiling alcohol having 1 to 4 carbon atoms, such as methanol, ethanol, propanol or butanol). The final silicone layer and the intermediate pore-protecting silicone layer should desirably have a total thickness in the range of from 500 to 5000Å and, more preferably, in the range of from 1000 to 2000Å.

The above procedure illustrates a process for producing an optically active aldehyde mixture having reduced metal content which comprises: (a) providing a crude hydroformylation reaction mixture, said reaction mixture comprising an optically active aldehyde mixture and an optically active metal-ligand complex catalyst and (b) passing the reaction mixture through a membrane comprising a porous substrate layer and a silicone layer to produce, as a permeate, an optically active aldehyde mixture containing a reduced amount of the metal.

Crystallization a. Solutions

Once the requisite mixture of enantiomeric aldehydes has been provided, the next step of the process of the present invention involves crystallizing the mixture from a solution thereof so as to isolate the desired enantiomer in a purer form. Suitable solutions can be provided by using liquid aldehydes or by melting solid aldehydes (when melt crystallization is employed). However, suitable solutions usually consist of the aldehydes dissolved in an appropriate solvent (e.g., in the solvent in which the first step of the process of this invention was conducted). Any solvent which will dissolve the aldehyde mixture may be used. Examples of suitable solvents are ketones (e.g., acetone), esters (e.g., ethyl acetate), hydrocarbons (e.g., toluene), nitrohydrocarbons (e.g., nitrobenzene) and ethers [e.g., tetrahydrofuran (THF) and glyme]. A mixture of two or more solvents can be employed to maximize the purity and yield of the desired aldehyde. The solution used may also contain materials other present in the crude reaction product of the aldehyde-forming reaction (e.g., catalyst, ligand and heavies). Preferably, however, the solution consists essentially of only the aldehyde mixture and the solvent. The concentration of the aldehyde mixture in the solvent solution will be limited by the solubility of the aldehyde mixture in the solvent.

b. Crystallization Conditions

In the process of the present invention the solution containing the enantiomeric aldehyde mixture is maintained under conditions such that the solubility limit of the desired aldehyde is exceeded. Such conditions include addition of a non-solvent to the solution, removal of any solvent from the solution and, preferably, cooling the solution. Combinations of these conditions can be used to effect the desired crystallization.

With respect to crystallization by using solvent removal, it should be noted that, if the pressure above the solution is fixed, then adding heat will increase solution temperature until the solution boils. Upon continued addition of heat, solvent will evaporate and the solution will become saturated. At this point, the solution concentration will remain constant (Gibbs Phase Rule) and continued heating will precipitate (crystallize) solute (i.e., the desired aldehyde). Conversely, if the pressure above the saturated solution which exhibits an increase in solubility with increased temperature is slowly reduced, the temperature of the solution will decrease and cooling will cause precipitation (crystallization) of solute (i.e., the desired aldehyde).

With respect to crystallization by using non-solvent addition, it should be noted that adding a liquid to the saturated solution that is miscible with the solvent but in which the solute has limited solubility will cause the solute (i.e., the desired aldehyde) to precipitate (crystallize).

Although the description of the present invention appearing below relates primarily to crystallization by cooling, this invention encompasses any conditions for effecting the desired crystallization.

c. Phase Diagrams

The present invention is applicable to the separation of any enantiomeric aldehyde (first aldehyde) from an mixture containing that aldehyde and the corresponding enantiomeric aldehyde, provided the mixture is in the compositional region where only the first aldehyde crystallizes on cooling of solution of the mixture. Suitable mixtures include mixtures of conglomerate aldehyde compounds (illustrated by FIG. 2 which is discussed below) and mixtures of aldehydes that can form racemic compounds (illustrated by FIG. 3 which is discussed below).

Figure 2:
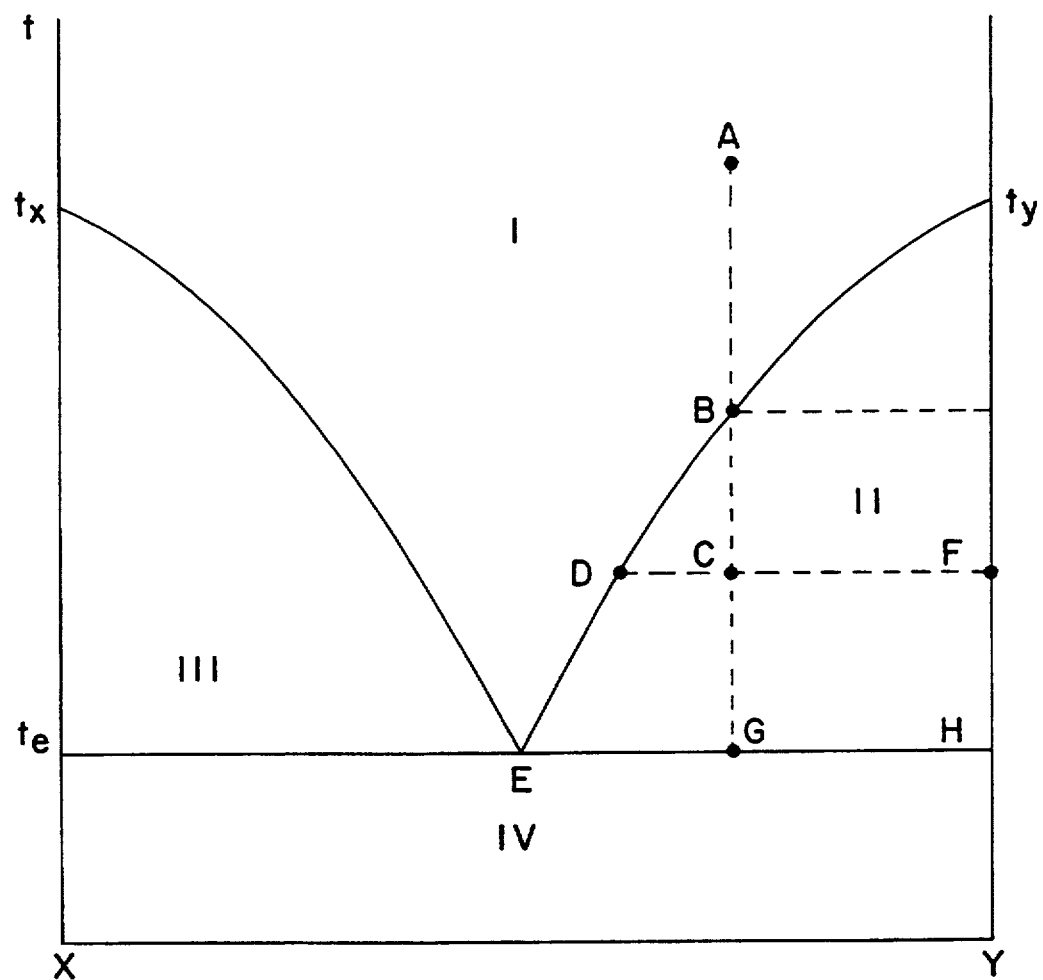
FIG. 2 is a phase diagram illustrating the phenomena involved in the practice of the present invention when conglommerates are involved.

When aldehydes being separated are conglomerates, the crystallization phenomenon that occurs in the practice of the present invention is generally governed by the factors illustrated in FIG. 2 which is a phase diagram of two substances, X and Y (e.g., enantiomer aldehydes). In FIG. 2, area (i.e., compositional region) I represents a unsaturated solution containing X and Y, area (i.e., compositional region) II corresponds to the coexistence of crystals of substance Y and the saturated solution containing X and Y, area (i.e., compositional region) III represents the coexistence of crystals of substance X and the saturated solution containing X and Y, and area (i.e., compositional region) IV corresponds to mixtures of crystals of substances X and Y. The curve separating areas (i.e., compositional regions) I and II is the solubility curve for substance Y, while the curve separating areas (i.e., compositional regions) I and III is the curve for phase equilibrium between solid X and the corresponding solution containing X and Y. The curves intersect at point E, where solid X, solid Y and a solution with composition E, that is saturated with both X and Y are in equilibrium. Points $t_x$ and $t_y$ are the melting points of pure components X and Y, respectively.

If an unsaturated solution containing X and Y (represented by point A in FIG. 2) is cooled, the composition of the solution does not change and the point representing the cooling solution therefore moves vertically downward on the phase diagram (FIG. 2). With continued cooling, this vertical line intersects the solubility curve at point B, lying on the boundary of the region corresponding to the separation of crystals of substance Y. On still further cooling, crystals of only substance Y separate, the solution is depleted in component Y and hence the composition of the solution moves along the solubility curve from right to left. For example, on cooling the solution down to a temperature corresponding to point C, crystals of composition F and the mother liquor (melt or solution) with a composition corresponding to point D are in equilibrium in the weight ratio $\overline{CD}$:$\overline{CF}$. On a further decrease in temperature, the point representing the liquid phase (solution) moves along the solubility curve towards point E. Finally, at a temperature corresponding to point G, crystals of H are in equilibrium with a solution of composition E. Solution E is saturated with both components, so that the crystals of both components will separate from a liquid phase (solution) with a constant composition at constant temperature $t_e$ on further removal of heat. Temperature $t_e$ is thus the lowest temperature at which crystals of a single component can still be obtained from the solution. For initial solution A, the weight ratio of the maximum obtainable amount of crystals of Y to mother liquor E is given by the ratio of segments $\overline{EG}$:$\overline{GH}$. Point E is called the eutectic point, temperature $t_E$ is the eutectic temperature and the mixture of substances X and Y with composition corresponding to point E is a eutectic mixture.

Figure 3:
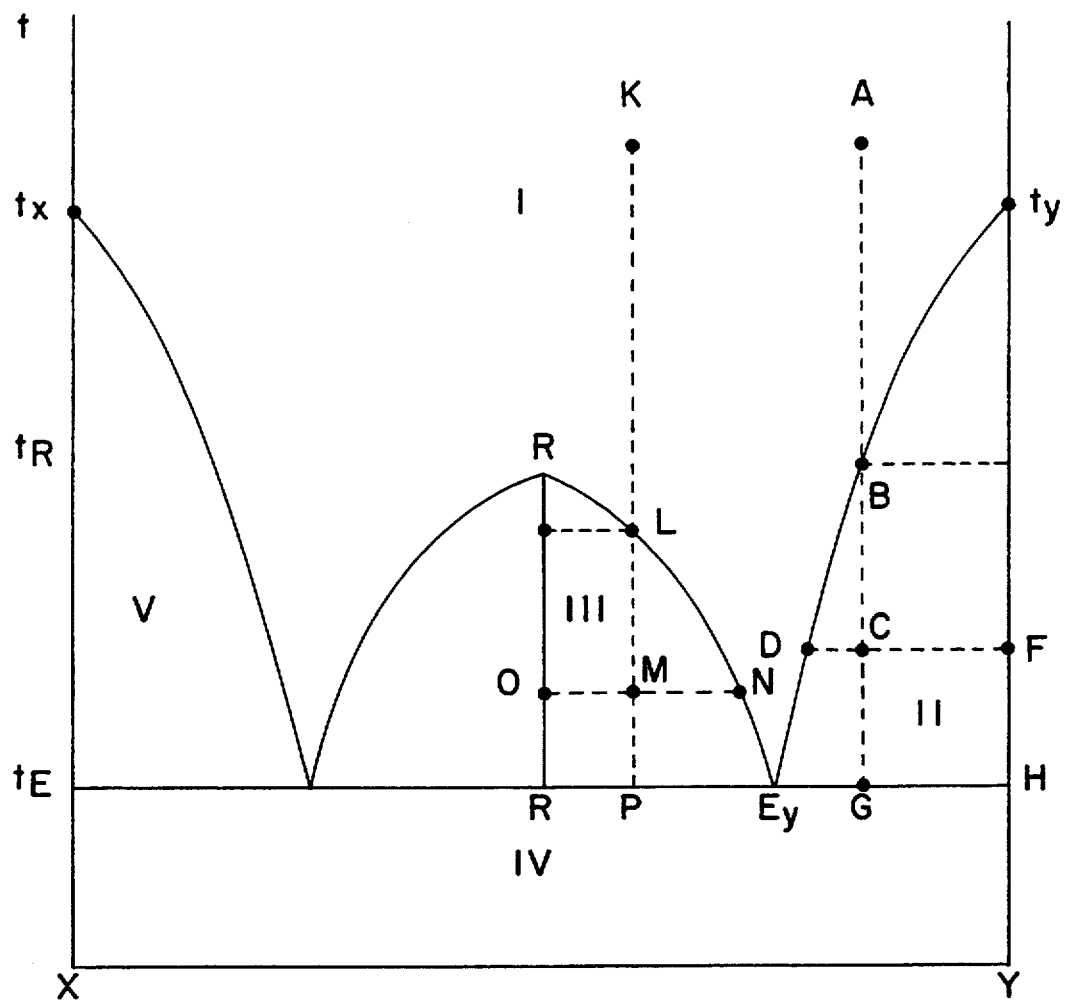
FIG. 3 is a phase diagram illustrating the phenomena involved in the practice of the present invention when racemic compounds are involved.

FIG. 3 is a melting point diagram (or phase diagram) of enantiomers that can form a racemic compound. The shape of such diagrams can vary within rather large limits depending upon whether the racemic compound melting point is greater, lower, or equal to that of the enantiomers. In FIG. 3, $t_R$ represents a racemic compound having a melting point that is lower than $t_Y$ (or $t_X$), which is the melting point of the pure optically active substance. The eutectic $E_Y$ (or $E_X$ consists of a mixture of crystalline Y (or X) and racemic compound R.

If a solution of X and Y having composition A in FIG. 3 is cooled to B, pure crystalline Y will begin to form. As the solution of composition B is cooled further, the composition of the solution follows the path from B to D to EY while continuing to form pure crystalline Y. Upon reaching solution composition $E_Y$ a mixture of crystalline pure Y and crystalline racemic compound R forms thereby limiting possibility of additional recovery of pure Y. Similarly, crystals of only X can be obtained by cooling solutions in area V (i.e., compositional region V).

If point K in FIG. 3 represents the initial solution composition, then cooling the solution to L initiates formation of racemic crystalline compound R. Upon Further cooling, the solution composition follows the path L to N to E$_Y$ while continuing to form crystalline racemic compound R. Upon reaching composition E$_Y$, a mixture of crystalline pure Y and crystalline racemic compound R forms. Thus, if K represents the initial solution composition, pure crystalline Y can not be obtained by cooling.

Thus, Areas II and V in FIG. 3 illustrate compositional regions in which the process of this invention can be practiced to produce relatively pure X (area V) or relatively pure Y (area II).

Although FIGS. 2 and 3 have been disclosed above in terms of crystallization achieved by cooling, the phase relationships shown in FIGS. 2 and 3 are also applicable to crystallization achieved by any other means.

d. Compositional Region

Initially, the appropriate concentration of the aldehydes in the solution (i.e., concentration in the region where only the desired enantiomer crystallines) can be achieved by controlling the above-described asymmetric syntheses, particularly by the proper selection of the chiral ligand used in the syntheses. By way of illustration, the following ligands have resulted in aldehyde mixtures in the desired compositional region when used in rhodium-catalyzed asymmetric hydroformylation of 6-methoxy-2-vinylnaphthalene to produce the aldehyde precursor for S-naproxen S-2-(6-methoxy-2-naphthyl)-propionaldehyde):

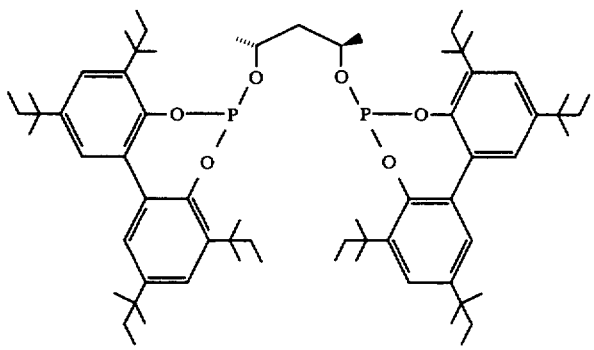

A

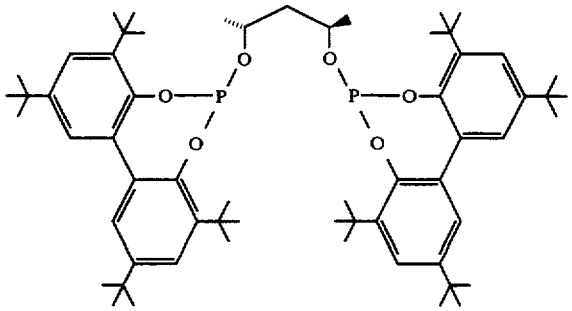

B

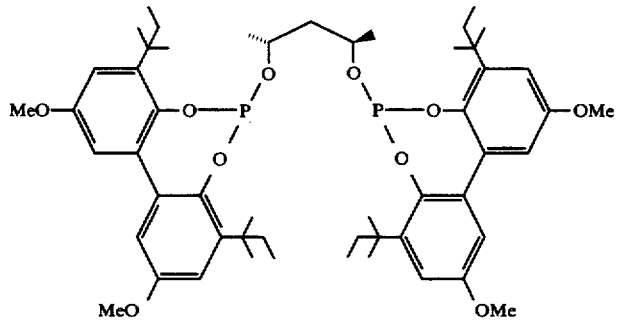

C

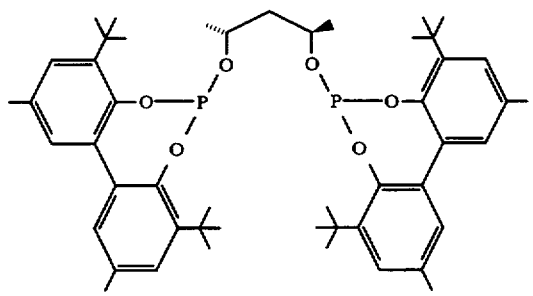

D

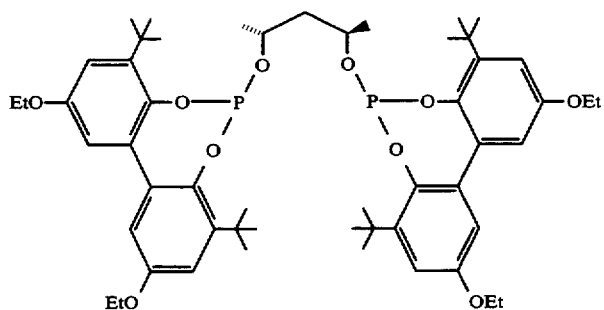

E

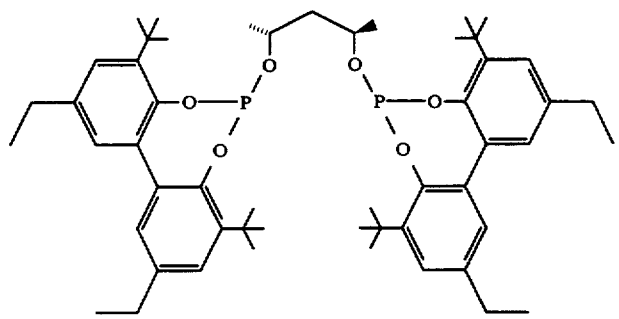

F

The results achieved with the above ligands were as follows:

| Ligand | Aldehyde Product b/n ratio* | ee** |
|---|---|---|
| A | 100:1 | 78% |
| B | 70:1 | 76% |
| C | 50:1 | 79% |
| D | 65:1 | 82% |
| E | 60:1 | 83% |
| F | 75:1 | 82% |

*Ratio of branched isomer to normal isomer.
**Enantiomeric excess.

The above hydroformylation reaction conditions were: 25° C., 130 psi, 1:1 $H_2/CO$, 300 ppm Rh, 2:1 ligand/Rh ratio and an acetone solvent.

The second step of the process of the present invention (crystallization) is conducted using solutions containing non-eutectic aldehyde mixtures in the compositional region where only the desired aldehyde is obtained by crystallization. During crystallization by cooling, the relative concentration of the enantiomeric aldehydes, the uniformity of solution temperature, the cooling rate and the cooling temperature are controlled so that the concentration of the aldehydes remains in the region where only the desired enantiomer crystallizes. Thus, with reference to FIG. 1, in order to crystallize only component Y, the relative concentration of the enantiomers must be controlled to be to the right of eutectic concentration (E). During the crystallization (when the concentration of Y in the solution shifts to the left on the solubility curve toward the eutectic concentration, E), the appropriate concentration is maintained by stopping crystallization before the eutectic concentration and/or temperature are reached.

The enantiomeric aldehyde mixtures useful in the process of this invention can have any composition other than the composition at which the mixture is eutectic (i.e., the mixtures are non-eutectic), provided the composition is in the region where only the desired aldehyde crystallizes on cooling the mixture. The reason for the requirement of using non-eutectic mixtures is that unacceptably large amounts of the undesired enantiomer usually crystallize from eutectic mixtures.

e. Crystallization Temperature

In the preferred practice of the process of the present invention, solutions containing the enantiomeric aldehyde mixtures are cooled to effect crystallization of the desired enantiomer. Higher crystallization temperatures promote the formation of desirably larger crystals but increase the possibility of undesirable racemization. The temperature of the solution can be raised slightly after the crystals initially form to a temperature just below the initial crystallization temperature and then the temperature can be lowered again. This technique causes the smaller crystals to redissolve and the larger crystals to grow still larger with the result that better generation of the crystals from the solution is achieved. Crystallization temperature will effect both product purity and yield in that lower temperatures produce higher yields.

f. Crystallization In Stages

In the preferred practice of the process of the present invention, the crystallization can, if desired, be conducted by cooling in stages. That is, the initial solution of the aldehyde mixture can cooled to a temperature at which the desired aldehyde crystallizes and held at that temperature until crystallization is complete. Then the crystals can be filtered from the remaining solution to produce a filtrate and the filtrate can be again cooled to crystallize additional amounts of the desired aldehyde. The cooling-crystallization-filtration-cooling sequence can be repeated as often as desired, provided the eutectic composition and temperature are not reached. The advantage of operating in stages is increased yield of the desired aldehyde. It is desirable to remove some of the solvent between each cooling stage.

g. Crystallization Apparatus

In the practice of the present invention, the crystallization of the desired enantiomeric aldehyde can be achieved using any convenient apparatus. The preferred apparatus is a falling film crystallizer such as is disclosed in U.S. Pat. No. 3,621,664 and that apparatus contains vertical (usually metallic) wall surfaces which are cooled from the opposite wall surface. When the liquid phase (i.e., the solution of the aldehyde mixture) flows as a much smaller stream-like film that is spread over the area of the wall, the separation is superior to that obtained when the liquid phase fills the entire cross section of the means, such as a pipe, down which it flows, the wetted circumference and the quantity of flow for the one case being equal to those of the other. The reason for this is that in the case of the film the flow is turbulent, whereas in the other case, for a given example, the flow has a Reynolds Number of 1600, indicating a laminar flow. The turbulent flow in the falling film has a laminar boundary layer a few tenths of a millimeter thick where mass transfer occurs by molecular diffusion, whereas this boundary layer for a completely laminar flow is approximately ten millimeters thick. The equation for the actual distribution coefficient, reproduced in "Background of the Invention" in U.S. Pat. No. 3,621,664, shows that a distribution coefficient approaching the best possible value is obtainable with film flow, when the crystallization rate is on the order of one centimeter per hour, as would be required in a large scale operations and, when the molecular diffusion coefficient in the liquid phase is on the order of $10^{-5}$ centimeters$^2$/second; whereas in the other case the distribution coefficient is close to one, indicating virtually no separation. If good separation is wanted in the other case, the Reynolds Number must be raised, which necessitates a larger flow and greater power consumption, particularly with viscous liquids, rendering operation uneconomical.

Good separation of the desired enantiomeric aldehyde during crystallization occurs in the apparatus of U.S. Pat. No. 3,621,664 even in the laminar region, provided that the waves appearing on the film surface cause a mixing action. Here also the layer thickness is only a few tenths of a millimeter and separation is correspondingly good. The quantity of liquid processed and the power consumed by the circulation pump are relatively little. The cooled vertical walls of the crystallizer are, in a preferred embodiment, in the form of tube bundles having any desired number of vertical, parallel tubes, the liquid being introduced at the tops of the tubes by a distributor to flow down the tubes inner surfaces as a film, and the cooling medium filling the jacket surrounding the tubes. The lower end of the crystallizer incorporates a tank for collecting the liquid phase.

The desired aldehyde crystals usually form on the inner surface of the falling film crystallizer. The crystals are removed by dissolving the crystals in a solvent (e.g., acetone) at a temperature below the melting point of the desired crystals to avoid substantial racemization of the desired crystals.

Two other arrangements of the apparatus of U.S. Pat. No. 3,621,664 can be used for crystallization in accordance with the present invention on an industrial scale. In one arrangement, crystallization occurs on the outer surfaces of a heat exchanger composed of a bundle of thin, parallel tubes, with baffle plates causing a strong cross flow of the liquid phase. In the other arrangement, the crystals form on the outer surface of a horizontal pipe grid, the liquid phase flowing down over the grid. In both arrangements, the cross flow about the pipes causes a turbulence producing a general mixing action, the laminar boundary layer at each pipe being then very thin. Similar results are obtained with cooled or, for some applications, heated short fins or baffle plates positioned in the flow to give a pronounced cross flow.

The separation in the preferred crystallization apparatus may be improved during crystallization by periodically briefly heating (or cooling, in certain applications) the fluid phase before it enters the crystallizer. This measure yields a smooth crystal surface and avoids dendritic or uneven crystal growth with the attendant undesirable trapping of mother liquid within the crystal layer.

Crystallization in the above-mentioned preferred crystallization apparatus is conveniently carried out in a single apparatus in such a manner that single crystallizations are cyclically repeated, beginning with the step of the highest concentration of impurity or impurities and advancing to the step of the desired component in its purest form. The small amount of mother liquor (i.e., solution of the aldehyde mixture) held on the surfaces of the crystallizer only slightly contaminates the crystallization of the succeeding step and going from the "purest" step to the "least pure" step, when ending one cycle and starting another, does not influence the separation.

The crystallization process can be conducted in the preferred crystallization apparatus in an inert atmosphere. The crystals of the final step can be further purified by distillation or partial melting and the less pure separated substance returned to the final step. The surface on which crystallization occurs can be cooled by flowing a heat exchange medium, in the form of a film, over the opposite surface of the crystallizer wall. This surface can be vertical, horizontal, or at any angle therebetween.

h. Product Purity

The crystals of the desired enantiomeric aldehyde produced by the process of the present invention contain considerably less of the other enantiomeric aldehyde than is contained the starting liquid aldehyde mixture. However, some of the other aldehyde may be present in the crystals due to occlusion, incomplete draining or entrainment of the solution from which the crystals are formed. Thus, the process of this invention provides optically active aldehydes having very high enantioselectivities and very high regioselectivities. With respect to enantioselectivity, enantiomeric excesses of preferably greater than 96%, and more preferably greater than 99%, can be obtained by the process of this invention. With respect to regioselectivity, branched/normal molar ratios of preferably greater than 100:1, more preferably greater than 200:1 and most preferably greater than 1000:1, can be obtained by the process of this invention. In addition, the desired aldehydes are relatively free of any residual metal catalyst (e.g., rhodium) used in the production of the starting aldehyde mixture, especially when the above-described membrane separation is employed. Thus, if the initial aldehyde solution contains substantial amounts of metal catalyst (e.g., 300 parts per million of rhodium), the desired aldehydes can contain less than 20 parts per million by weight of residual metal catalyst (e.g., rhodium) when crystallization without membrane separation is used. The desired aldehydes can contain less than 2 parts per million by weight of residual metal catalyst (e.g., rhodium) when membrane separation followed by crystallization is used.

Derivatives and Utility

The enriched, optically active aldehydes produced by the process of this invention can undergo further reaction(s) to afford desired derivatives thereof. Such derivatization reactions can be carried out in accordance with conventional procedures. Illustrative derivatization reactions include, for example, oxidation to carboxylic acids, reduction to alcohols, aldol condensation to alpha, beta-unsaturated compounds, reductive amination to amines, amination to imines and the like. This invention is not intended to be limited in any manner by the derivatization reactions. A preferred derivatization reaction involves oxidation of an optically active aldehyde prepared by asymmetric hydroformylation to give the corresponding optically active carboxylic acid. A number of important pharmaceutical compounds can be prepared by such derivatization processes process including, but not limited to, S-naproxen, S-ibuprofen, S-ketoprofen, S-suprofen, S-flurbiprofen, S-indoprofen, S-tiaprofenic acid and the like.

Illustrative of such derivatization reactions include, for example, reactions that involve the following reactant/aldehyde intermediate/product combinations:

| Reactant | Aldehyde Intermediate | Product |
| --- | --- | --- |
| 2-vinyl-6-methoxy-naphthalene | S-2-(6-methoxy-2-naphthyl)propionaldehyde | S-naproxen |
| 2-vinyl-6-methoxy-naphthalene | S-2-(6-methoxy-2-naphthyl)propionaldehyde | S-naproxen sodium |
| p-isobutylstyrene | S-2-(p-isobutylphenyl)-propionaldehyde | S-ibuprofen |
| 3-ethenylphenyl phenyl ketone | S-2-(3-benzoylphenyl)-propionaldehyde | S-ketoprofen |
| 4-ethenylphenyl-2-thienylketone | S-2-(p-thienoylphenyl)-propionaldehyde | S-suprofen |
| 4-ethenyl-2-fluoro-biphenyl | S-2-(3-fluoro-4-phenyl)-phenylpropionaldehyde | S-flurbiprofen |
| 4-(1,3-dihydro-1-oxo-2H-isoindol-2-yl)-styrene | S-2-[4-(1,3-dihydro-1-oxo-2H-isoindol-2-yl)-phenyl]propionaldehyde | S-indoprofen |
| 2-ethenyl-5-benzoyl-thiophene | S-2-(2-methyl-acetaldehyde)-5-benzoyl-thiophene | S-tiaprofenic acid |
| 3-ethenylphenyl phenyl ether | S-2-(3-phenoxy)propion-aldehyde | S-fenoprofen |
| propenylbenzene | S-2-phenylbutyraldehyde | S-phenetamid, S-butetamate |
| phenyl vinyl ether | S-2-phenoxy-propionaldehyde | pheneticillin |
| vinyl chloride | S-2-chloropropional-dehyde | S-2-chloro-propionic acid |
| 2-vinyl-6-methoxy-naphthalene | S-2-(6-methoxynaphthyl)-propionaldehyde | S-naproxol |
| 5-(4-hydroxy)benzoyl-3H-pyrrolizine | 5-(4-hydroxy)benzoyl-1-formyl-2,3-dihydro-pyrrolizine | ketorolac or derivative |
| 3-ethenylphenyl phenyl ketone | R-2-(3-benzoylphenyl)-propionaldehyde | R-ketoprofen |
| 4-ethenyl-2-fluoro-biphenyl | R-2-(3-fluoro-4-phenyl)-phenylpropionaldehyde | R-flurbiprofen |

The optically active derivatives of the products of the process of this invention have a wide range of utility that is well known and documented in the prior art, e.g. they are especially useful as pharmaceuticals, flavors, fragrances, agricultural chemicals and the like. Illustrative therapeutic applications, include, for example, nonsteroidal anti-inflammatory drugs, ACE inhibitors, beta-blockers, analgesics, bronchodilators, spasmolytics, antihistimines, antibiotics, antitumor agents and the like.

As used herein, the following terms have the indicated meanings:

Chiral—compounds which have a non-superimposable mirror image.

Achiral—compounds which do not have a non-superimposable mirror image.

Prochiral—compounds which have the potential to be converted to a chiral compound in a particular process.

Chiral center—any structural feature of a compound that is a site of asymmetry.

Racemic—a 50/50 mixture of two enantiomers of a chiral compound.

Stereoisomers—compounds which have identical chemical constitution, but differ as regards the arrangement of the atoms or groups in space.

Enantiomers—stereoisomers which are non-superimposable mirror images of one another.

Stereoselective—a process which produces a particular stereoisomer in favor of others.

Enantiomeric excess (ee)—a measure of the relative amounts of two enantiomers present in a product. ee may be calculated by the formula [amount of major enantiomer—amount of minor enantiomer]/[amount of major enantiomer + amount of minor enantiomer].

Optical activity—an indirect measurement of the relative amounts of stereoisomers present in a given product. Chiral compounds have the ability to rotate plane polarized light. When one enantiomer is present in excess over the other, the mixture is optically active.

Optically active mixture—a mixture of stereoisomers which rotates plane polarized light due to an excess of one of the stereoisomers over the others.

Optically pure compound—a single stereoisomer which rotates plane polarized light.

Regioisomers—compounds which have the same molecular formula but differing in the connectivity of the atoms.

Regioselective—a process which favors the production of a particular regioisomer over all others.

IsoBHA chloridite—1,1'-biphenyl-3,3'-di-t-butyl-5,5'-dimethoxy-2,2'-diylchlorophosphite.

(IsoBHA-P)₂—2R,4R-pentanediol—A ligand having the formula:

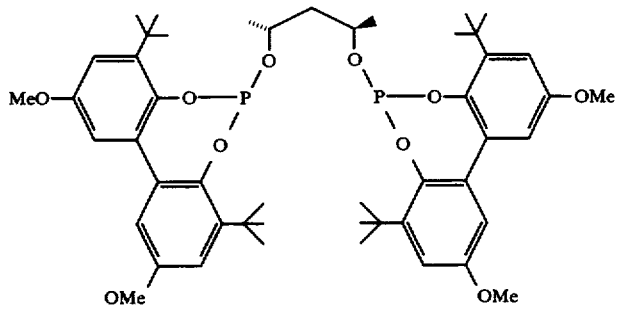

The latter ligand can be produced from Iso BHA chloridite by the process described in Example 1 of above-mentioned PCT Patent Application 93/03839. The complete chemical name of this ligand is (2R, 4R)-Di[2,2'-(3,3'-di-tert-butyl-5,5'-dimethoxy-1,1'-biphenyl)]-2,4-pentyl diphosphite.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all compounds having at least one hydrogen and one carbon atom. In a broad aspect, the hydrocarbons include acyclic and cyclic, branched and unbranched, carbocyclic and heterocyclic, aromatic and nonaromatic organic compounds which can be substituted or unsubstituted.

As used herein, the following symbols have the indicated meanings:

| | |
|---|---|
| L | liter |
| wt % | weight percent |
| mL/min | milliliters per minute |
| ppm | parts per million by weight |
| g | grams |
| psi | pounds per square inch |
| °C. | degrees centigrade |
| b/n | branched to normal isomer ratio |
| CC | cubic centimeter |
| DSC | Differential Scanning Calorimeter |
| GC | Gas Chromatographic |
| HPLC | High Performance Liquid Chromatography |

The following Examples are provided to illustrate the process of this invention.

EXAMPLE 1

Improving Enantiomeric Purity of an Aldehyde Through Crystallization in Acetone

A solution consisting of 6-methoxy-2-vinylnaphthalene (395 g), Iso(BHA-P)2-2R,4R-pentanediol (6.041 g), $Rh_4(CO)_{12}$ 0.862 g) and acetone (1500 ml) was charged to a 1 gallon reactor which was pressurized to 250 psi with 1:1 $H_2/CO$. The reaction mixture was stirred at ambient temperature for four days to effect hydroformylation. The crude reaction product so produced was removed from the reactor and an aliquot removed to determine the composition of the product.

GC analysis of the aliquot of the crude reaction product indicated that 98.8% of the olefin starting material had been converted to aldehydes and that a 95:1 ratio of 2-(6-methoxy-2-naphthyl)propionaldehyde to 3-(6-methoxy-2-naphthyl)propionaldehyde had been obtained. Oxidation of the aldehydes in the aliquot followed by chiral High Performance Liquid Chromatography (HPLC) analysis of the resulting carboxylic acids indicated that an 81% ee of the desired S-aldehyde [i.e., S-2-(6-methoxy-2-naphthyl)propionaldehyde] was produced.

The above-mentioned oxidation and HPLC analysis were conducted as follows: 3 ml of the crude reaction product was diluted in 50 ml of acetone and mixed with 0.3 g of potassium permanganate and 0.32 g of magnesium sulfate. The mixture so formed was stirred at room temperature for 30 minutes to effect oxidation of the aldehydes in the crude reaction product to the corresponding carboxylic acids. Then the acetone was removed under reduced pressure. The residue so produced was extracted three times with 50 ml of hot water and the three aqueous solutions so obtained were combined, filtered and washed with 50 ml of chloroform. The aqueous layer was then acidified with HCl to a pH of 2 at which time a white, solid precipitate formed. The precipitate was filtered, washed with water and dried to isolate the carboxylic adds. The carboxylic adds were analyzed by chiral HPLC on a CHIRACEL TM OD-H column which could separate the two enantiomers of the resulting 2-(6-methoxy-2-naphthyl)propionic acid.

The remainder of the crude reaction product was stored at −22° C. overnight and during that time crystals formed. These crystals were filtered, washed with cold acetone and dried under vacuum to yield 111 g of off-white crystals and a first filtrate. Analysis of the crystals indicated that the b/n isomer ratio had been increased to a >250:1. Oxidation of the aldehydes to carboxylic adds and chiral HPLC of the resulting carboxylic adds indicated a 93% ee of the S-enantiomer had been obtained.

The first filtrate was stored overnight at −22° C. and additional crystals formed. These crystals were filtered, washed with cold acetone and dried under vacuum to yield a second filtrate and 70 g of white crystals with an b/n isomer ratio of 250:1 and a 93% ee of the S-enantiomer.

The second filtrate was stored at −22° C. overnight and again crystals formed. Filtration, washing and vacuum drying of these crystals resulted in isolation of 50 g of a crystalline aldehyde product having an b/n isomer ratio of 200:1 and an ee of 92% S-enantiomer.

EXAMPLE 2

Improving Enantiomeric Purity of Aldehydes Through Crystallization in Ethyl Acetate A solution consisting of 6-methoxy-2-vinylnaphthalene (60 g), Iso(BHA-P)$_2$-2R,4R-pentanediol (1.25 g), Rh$_4$(CO)$_{12}$ (0.131 g) and ethyl acetate (180 g) was charged to a 300 ml reactor which was pressurized to 250 psi with 1:1 H$_2$/CO. The reaction mixture so formed was stirred at ambient temperature for four days to effect hydroformylation. The crude reaction product was removed from the reactor and an aliquot removed to determine the composition of the product.

GC analysis of the aliquot indicated that 99% of the olefin starting material had been converted to aldehydes and that a 59:1 ratio of 2-(6-methoxy-2-naphthyl)propionaldehyde to 3-(6-methoxy-2-naphthyl)propionaldehyde had been obtained. Oxidation of the aldehyde products followed by chiral HPLC analysis of the resulting carboxylic acids indicated that an 80% ee of the desired S-aldehyde [i.e., S-2-(6-methoxy-2-naphthyl)propionaldehyde] was produced.

The remainder of the crude reaction product was then stored at −22° C. overnight, during which time crystals formed in the container. These crystals were filtered, washed with cold acetone and dried under vacuum to yield 32 g of off white crystals. Subsequent analysis of these crystals indicated that the b/n isomer ratio had been increased to >129:1. Oxidation of the crystalline aldehyde and chiral HPLC of the resulting carboxylic acid indicated a 92% ee of the S-enantiomer had been obtained.

EXAMPLE 3

Membrane Separation of An Aldehyde from Acetone Solution

A. A crude hydroformylation reaction product similar to the crude reaction product produced in Example 1 above was processed through a membrane to remove the rhodium and ligand. The crude reaction product contained S-2-(6-methoxy-2-naphthyl)propionaldehyde (30 wt%) dissolved in acetone (70 wt%). The crude reaction product also contained rhodium (263.3 ppm) and ligand.

Figure 4:
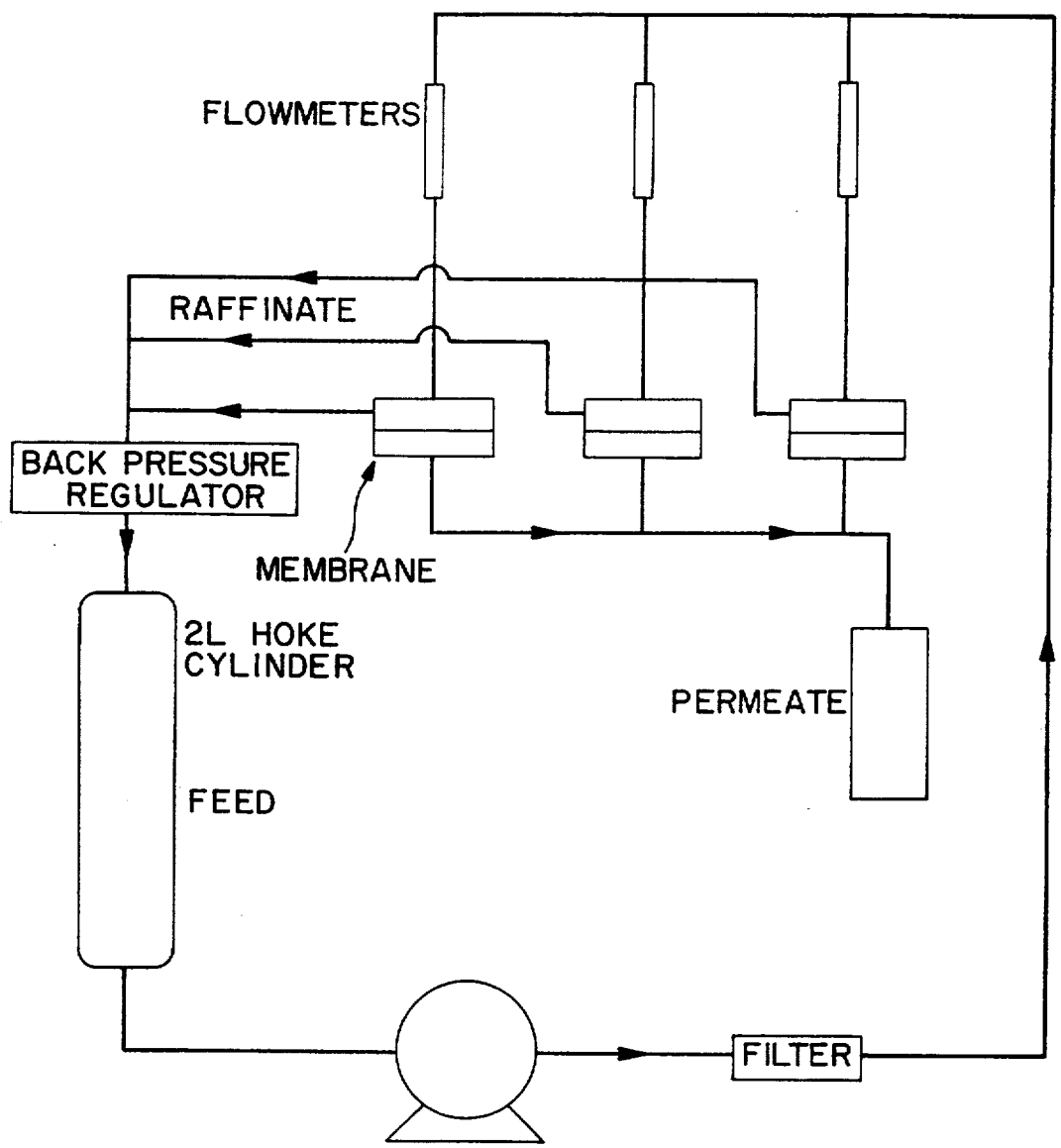
FIG. 4 shows a membrane and associated equipment useful in the practice of the present invention.

The membrane and associated equipment is shown in FIG. 4. The membrane was arranged and used as follows: Three 2 inch circles were cut from an 8 inch ×11 inch sheet of MPF-50 membranes (Lot #021192, code 5107) which are sold by Membrane Products Kiryat Weizmann Ltd. and which are believed to be within the scope of above-mentioned European Patent Application 0 532,199 A1. These circles were placed into three Osmonics membrane holders. The crude reaction product (feed) was placed into a 2L Hoke cylinder under nitrogen. The feed was pumped to 500 psi at a flow rate of about 380 mL/min. The feed flowed through a 60 micron filter and then was split into three streams which went to the membranes. Flowmeters were used to ensure that the flow was split equally to the holders. The permeate from the membranes was combined and collected under nitrogen. The raffinate flowed to a back pressure regulator and was then returned to the Hoke cylinder.

About 1500 g of the crude reaction product was permeated and the rhodium content of the resulting first permeate was about 69.4 ppm. The membrane and equipment were washed with acetone and the acetone was discarded.

The above-described membrane separation was repeated on the 1500 g of the first permeate (which contained 69.4 ppm rhodium) and 1000 g of a solution (containing 19.2 ppm rhodium) was separated as a second permeate. The composition of the second permeate was 80% acetone and 20% solids. The b/n isomer ratio of the solids was 64:1 and it contained 1.4% normal isomer, 9.9% R isomer, and 88.7% S isomer [i.e., S-2-(6-methoxy-2-naphthyl)propionaldehyde]. The enantiomeric excess (ee) of the crystalline solids was 80.7%. The second permeate so obtained was then concentrated and crystallized as described below.

A portion of the second permeate produced as described above was concentrated by evaporating acetone at 18° C. and 25 inches of mercury pressure to produce a concentrated solution containing 70% acetone and 30% solids. The concentrate so obtained was charged into the crystallizer shown in FIG. 5. The crystallizer consisted of a jacketed, 250 cc vertical cylinder (A) fitted with a stirrer (B) and an internal filter (C). Crystallization was initiated by cooling the jacket to −14° C. thus cooling the contents of the cylinder to near −14° C. In order to dissolve the small crystals that formed on the inner surface of the cylinder and to enhance crystal size, the crystallizer was reheated to 3° C. and again cooled to −14° C. using cooler (D). This procedure was repeated three times. Since the internal filter (C) clogged, the solid crystals formed in the cylinder and liquid were removed from the crystallizer and separated in a laboratory vacuum filter. The resulting filter cake was washed with one part by weight of cold acetone (0° C.) per two parts (by weight) of wet solids (filter cake). The resultant crystalline filter cake contained 13% acetone and 87% crystalline solids and had a b/n isomer ratio of 386:1. The solids contained 0.3 normal isomer, 2.4% R isomer and 97.3%S isomer. The enantiomeric excess of the solids was 95.2%. Scanning Electron Microscope (SEM) photos indicated that solid particles were uniform and about 100 microns in size.

B. The concentration and crystallization procedure of A above was repeated with another portion of the second permeate obtained in the above-described membrane separation and the crystals produced had a b/n isomer ratio of 446:1 and contained of 0.2% normal isomer, 2.7% R isomer, and 97.1%S isomer. The ee of the crystals was 94.6%.

C. The wet filter cakes produced via the procedures of A and B above were combined and dissolved in two parts by weight of acetone per part by weight of the combined wet filter cake. The solution so obtained was crystallized using the crystallization procedure of A above, separated and washed per the procedure of A above. The resultant crystals had a b/n isomer ratio of 921:1 and contained 0.1 normal isomer, 1.3%R isomer, and 98.6% S isomer. The ee of the crystals was 97.4%.

D. The wet crystalline filter cake produced by procedure of C above was dissolved in two parts (by weight) of acetone per part of the combined wet cake and crystallized using the crystallization procedure of A above, separated and washed according to the procedure of A above. The final crystals so obtained had a b/n isomer ratio of 1836:1. The crystal contained 0.05% normal isomer, 0.6%R isomer, 99.35%S isomer and 4 ppm rhodium. The ee of the crystals was 98.8%. The melting point of the crystals was 72.5° C. determined in a Differential Scanning Calorimeter (DSC).

EXAMPLE 4

Refining An Aldehyde from Ethyl Acetate Solution

A. A crude hydroformylation reaction product was used that was similar to the crude reaction product produced in Example 2 above and that was composed of 62.9% ethyl acetate and 37.1% solids containing S-2-(6-methoxy-2-naphthyl)propionaldehyde. The solids had a b/n of 42:1 were composed of 2.3% normal isomer, 11.7% R isomer and 86% S isomer [i.e., S-2-(6-methoxy-2-naphthyl)propionaldehyde] and had an ee of 76%. The crude reaction product was crystallized as follows:

B. Seven successive 250 cc charges of the crude reaction product were cooled to −7° C. in the crystallizer used in Example 3 above (see FIG. 5). The crystals and liquid resulting from the crystallization were separated on an external vacuum filter and the crystals were washed with 0.5 parts of ethyl acetate per part of wet cake. The resultant composite cake from the seven crystallizations contained 24% ethyl acetate and 76% crystalline solids. The b/n isomer ratio of the crystalline solids was 123:1 and the solids contained 0.8% normal isomer, 6.0% R isomer, and 93.2% S isomer. The ee of the crystalline solids was 87.9%.

Figure 5:
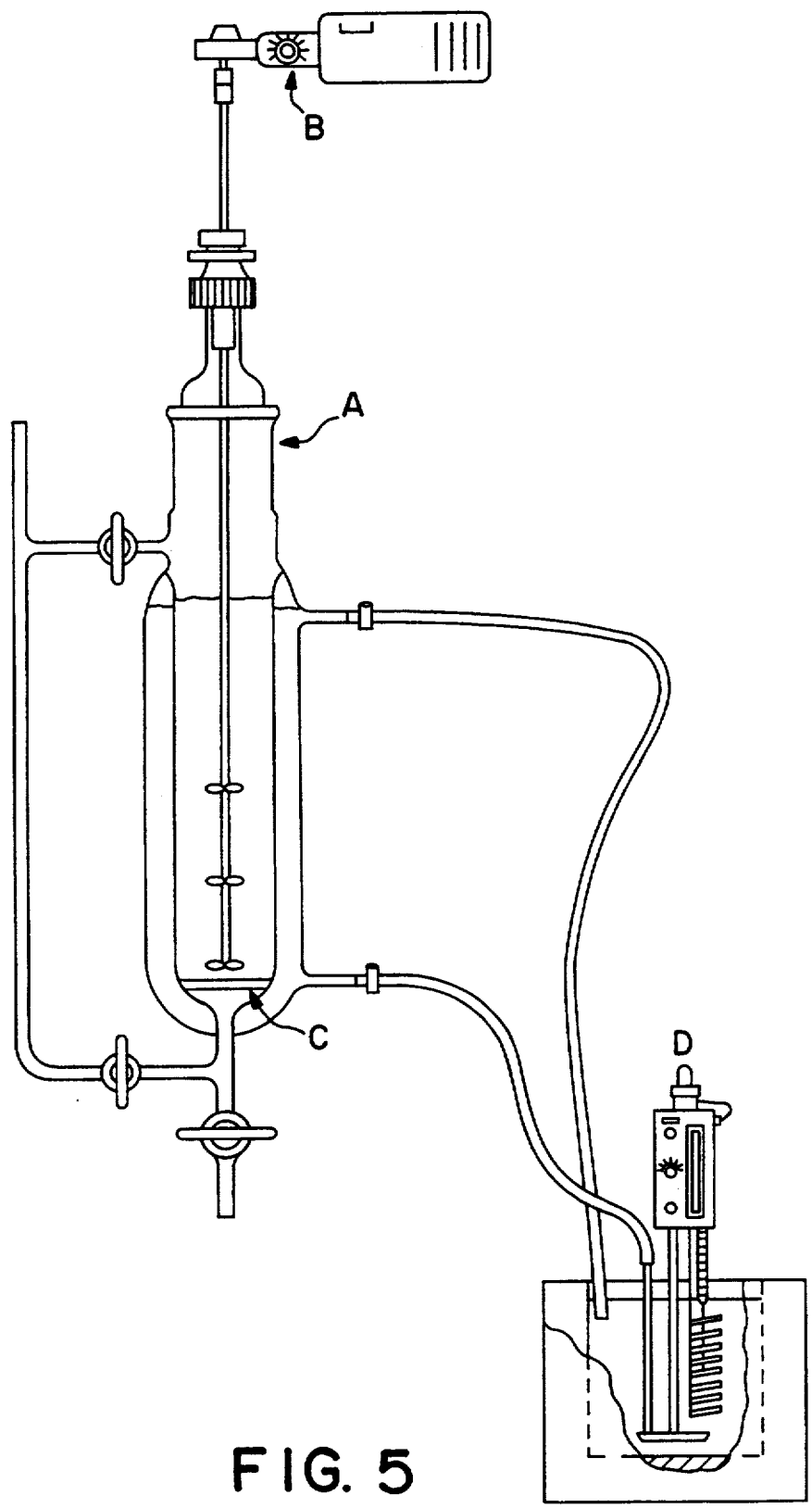
FIG. 5 shows a crystallizer useful in the practice of the present invention.

C. The wet filter cake from step B. above was dissolved in two parts by weight of ethyl acetate per part (by weight) of wet filter cake. The solution was cooled to −13° C. in the laboratory crystallizer (FIG. 5). The contents of the crystallizer were then reheated to 3° C. and again cooled to −13° C. This cool-reheat cycle was repeated two times to enhance the crystal size. The solid-liquid mixture so produced was separated in an external vacuum filter and the wet filter cake 50 produced was washed with 0.5 parts of cold (−10° C.) ethyl acetate per part of wet filter cake. The resultant cake contained 25% ethyl acetate and 75% crystalline solids. The crystalline solids had a b/n isomer ratio of 483:1 and had, a normal isomer content of 0.2%, an R isomer content of 1.6% and an S isomer content of 98.2%. The ee of the crystalline solids was 96.8%.

EXAMPLE 5

Refining of An Aldehyde from Acetone Solution in a Falling Film Crystallizer

Crude hydroformylation reaction product that was similar to the crude reaction product produced in Example 1 above and that contained 70% acetone and 30% solids was refined in a laboratory falling film crystallizer. The solids in the crude reaction product had a b/n isomer ratio of 69:1 and the solids composition was 1.4% normal isomer, 8.9% R isomer, and 89.7%S isomer [i.e., S-2-(6-methoxy-2-naphthyl)propionaldehyde]. The enantiomeric excess of the solids was 81.9%.

The crude reaction product was concentrated by evaporating 30% by weight of the solution. The resulting concentrate consisted of 57% acetone and 43% solids. This was crystallized in a laboratory falling film crystallizer by the following procedure.

Figure 6:
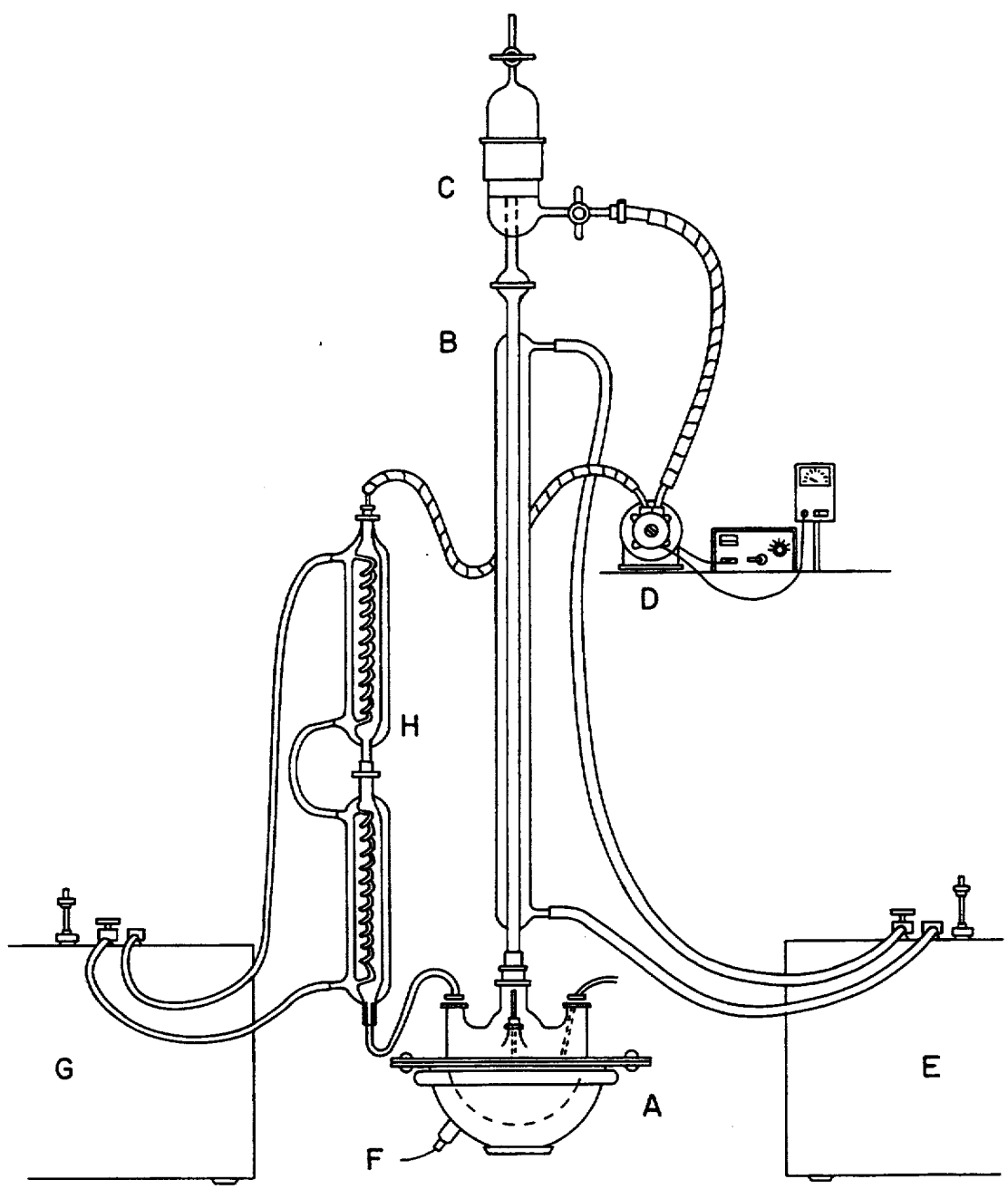
FIG. 6 shows another crystallizer useful in the practice of the present invention.

The crystallizer used is shown in FIG. 6 and consisted of a kettle (A), a jacketed column (B) {the column was a one meter long jacketed vertical tube having a one inch diameter internal opening} and (D) means for pumping (i.e., circulating) liquid from the kettle to the film device (C) at the top of the falling film crystallizer. The jacket of the crystallizer was affixed to a supply of coolant (E) which flowed co-current with the falling film. That is, both the falling film and the coolant in the jacket flowed downward in a co-current fashion. The crystallizer shown in FIG. 6 is similar in principle of operation to those described in above-mentioned U.S. Pat. No. 3,621,664.

Two thousand milliliters of the concentrate produced as described above were charged to the kettle (A) of the falling film crystallizer (FIG. 6). The concentrate in the kettle was circulated briefly down through the column (B) to wet the inside walls and then circulation was discontinued. Since the walls of the column were maintained at −20° C. by circulating coolant, a thin frosting of solids quickly formed on the inner walls of the column. The flow through the falling film crystallizer was resumed depositing crystals on the inside of column wall. After the kettle temperature was reduced to −16° C., the recirculation flow was stopped. During the cooling, a slight amount of heat was added to the kettle by a heating mantle (F) to prevent crystallization in the kettle. To compensate for this heating, the recirculating liquid was cooled slightly by circulating coolant from bath (G) to coolers (H). After crystallization was complete, the residual liquid in the kettle was emptied and the solids inside the crystallizer walls were washed with 50 cc of wash liquid that was added from the top of the column and this wash liquid was discarded. The composition of the kettle residue was 61% acetone and 39% solids. The solids in the kettle had a b/n isomer ratio of 60:1 and contained 1.6% normal isomer, 12.8%R isomer and 85.6%S isomer. The ee of the kettle solids was 74.0%.

600 cc of reagant grade acetone was added to the kettle and circulated to the falling film device at 20° C. and then down the inside wall of the column to dissolve the solids adhering to the inside of the column. This was a very quick and efficient technique for recovering adhering solids and is a unique method for recovery of solids from the falling film crystallizer. In the prior art, the internal film of crystals in such crystallizers is normally melted (see above-mentioned U.S. Pat. No. 3,621,664). However, the present invention is designed to increase the amount of the desired enantiomeric aldehyde (in this Example, the S-isomer) and melting is not feasible since the S-isomer will quickly racemize at its melting point (72.5° C.) and so the ee of the crystals will deteriorate.

The acetone solution recovered from the column wall contained 78% acetone and 22% crystalline solids. The crystalline solids had a b/n isomer ratio of 111:1 and contained 0.9% normal isomer, 6.9%R isomer and 92.2%S isomer. The crystalline solids ee was 86.1%.

EXAMPLE 6

Three 2 inch circles from an 8.5 inch×11 inch sheet of MPF-50 membranes (LOT #021192 code 5102). These were placed into three Osmonics membrane holders. Feed was placed into a 2 L Hoke cylinder under nitrogen in equipment arranged as shown in FIG. 4. The feed was pumped to 500 psi at a flow rate of about 380 ml/min. The feed flowed through a 60 micron filter and then was split into three streams which went to the membranes. Flowmeters were used to ensure that the flow was split equally. The permeate from the membranes was combined and collected under nitrogen. The raffinate flowed to a back pressure regulator and then was returned to the Hoke cylinder.

The feed was a 4 L batch of a crude hydroformylation reaction product containing 2-(6-methoxy-2-naphthyl)propionyldehydes (30 wt%) in acetone (70 wt%). The mixture also contained rhodium (389.3 ppm) and Iso(BHA-P)2-2R,4R-pentanediol. About 3325 g of this solution was permeated through the membrane and the resulting permeate solution had a rhodium content about 36.3 ppm. The system was emptied, cleaned with acetone and the waste discarded.

The 3325 g of the permeate solution containing 36.3 ppm rhodium was placed back into the Hoke cylinder and about 1439 g of this solution was again permeated through the membrane. The resulting permeate solution contained about 5.6 ppm rhodium.

The 1439 g of the solution containing 5.6 ppm rhodium was placed back into the Hoke cylinder and passed back through the membrane for the third time. About 935 g of this solution was permeated through the membrane and the resulting permeate had about 1.2 ppm rhodium. This permeate was then used as a feed for the crystallization process described below.

Figure 11:
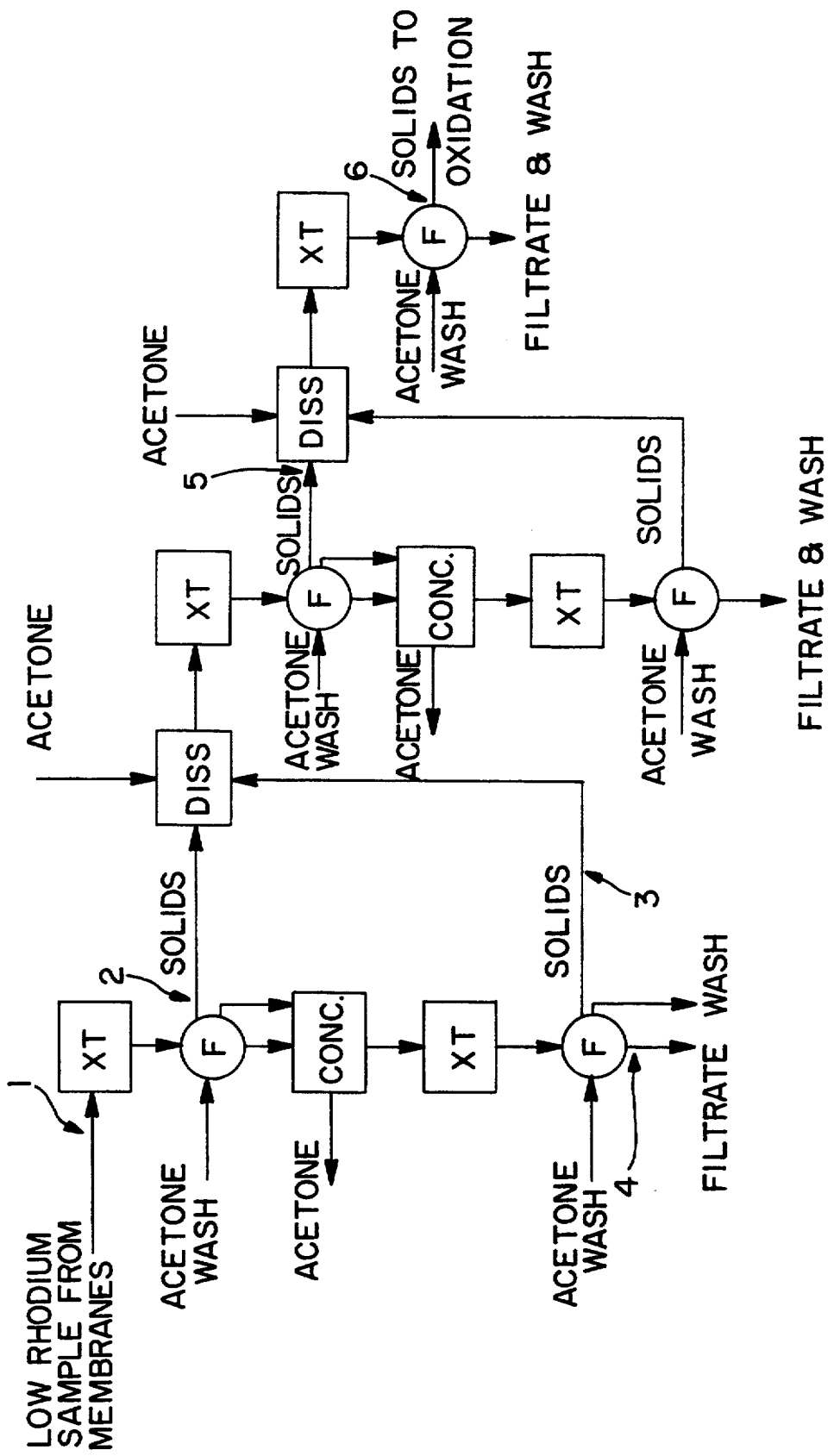
FIG. 11 is a flow diagram illustrating a preferred crystallization scheme that can be employed in the practice of the present invention.

Recovery and refining of S-2-(6-methoxynaphthyl)-propionaldehyde aldehyde from the permeate obtained as described above was accomplished by the sequence of operations depicted in FIG. 11. In summary, the permeate feed solution was batch crystallized by cooling to −10° C. The slurry so obtained was filtered to remove crystals and the crystals were washed with one half gram of acetone per gram of wet solids. The filtrate and was were combined and the solution concentrated to 40 percent solids by evaporating acetone. The crystallization, filtration and washing was repeated on this concentrated solution. The crystals from this second stage were combined with crystals from the first crystallization and dissolved in one and one half parts by weight of acetone per part of wet solids. This solution was processed in the same manner as the original permeate feed solution. The solids that were recovered and washed from both crystallization stages were again combined and dissolved in acetone. The final recrystallization was also conducted in the manner as described above in this Example. The refined crystalline solids from this last stage represented the final product (i.e., S-2-(6-methoxy-2-naphthyl)propionaldehyde). The final ee was 96.8. The yield of S-2-(6-methoxy-2-naphthyl)propionaldehyde as a fraction of that supplied in the feed was 26.8 percent.

EXAMPLE 7

A. Naproxen Aldehyde Melting Point Diagram

Figure 7:
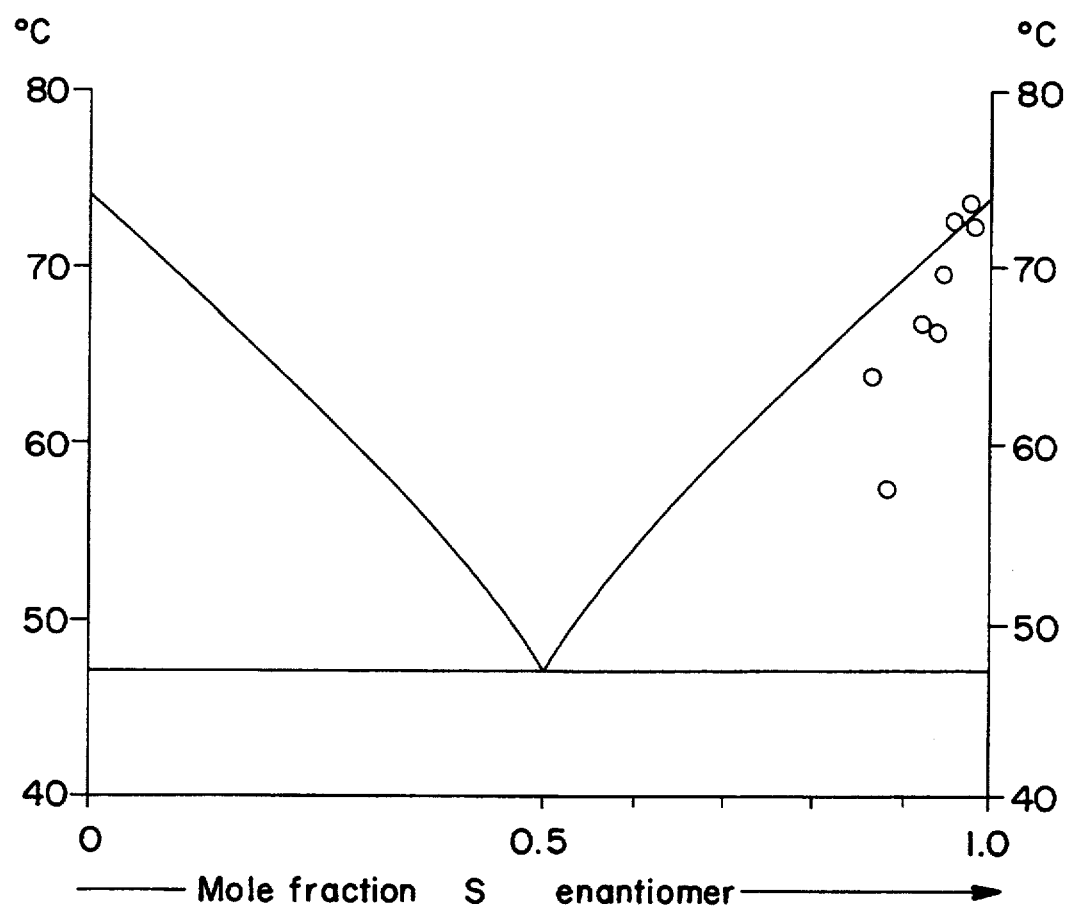
FIG. 7 is a melting point diagram for R- and S-2-(6-methoxy-2-naphthyl)propionaldehyde.

FIG. 7 is a melting point diagram for "Naproxen aldehyde" enantiomers S-2-(6-methoxy-2-naphthyl)propionaldehyde. The liquidus curves in FIG. 7 were calculated using the Schroder-Van Laar equation [see Jacques, J., A. Collet, and S. H. Wilen, "Enantiomers, Racemates, and Resolutions"; Kriegar (1991) p. 46]using 74° C. as the melting point of the pure isomers and 5630.4 calories per gram mole for the enthalpy of fusion. The assumptions in the Schroder-Van Laar equation include immiscibility of enantiomers in the solid state and ideality of the enantiomer mixture in the liquid state.

Experimental data was obtained using the crystallizer shown in FIG. 5 and is indicated in FIG. 7 as circles. Samples were obtained during crystallization tests in acetone solutions. The solid samples were removed from the slurry by filtration. The samples were then slowly heated in a Perkin/Elmer DSC7 to obtain the melting point. The data on FIG. 7 are tabulated on Table 1.

The melting point of pure S enantiomer S-2-(6-methoxy-2-naphthyl)propionaldehyde is discernible. It is difficult to develop a complete liquidus curve for a variety of reasons. A problem with melting point determination of such solid samples is that N isomer is present in sufficient concentration to depress the mixture melting point.

TABLE 1

Naproxen Aldehyde Melting Point Data

| Sample Composition | | | |
|---|---|---|---|
| % S | % R | % N | Melting Point, ° C. |
| 98.2 | 1.7 | 0.1 | 73.5 |
| 94.3 | 5.0 | 0.7 | 66.1 |
| 98.2 | 1.6 | 0.2 | 72.7 |
| 94.8 | 4.7 | 0.5 | 69.4 |
| 87.4 | 10.8 | 1.8 | 63.7 |
| 95.5 | 4.0 | 0.5 | 72.5 |
| 88.1 | 8.7 | 3.2 | 57.2 |
| 92.3 | 7.0 | 0.7 | 66.9 |

B. Naproxen Aldehyde Solubility

Figure 8:
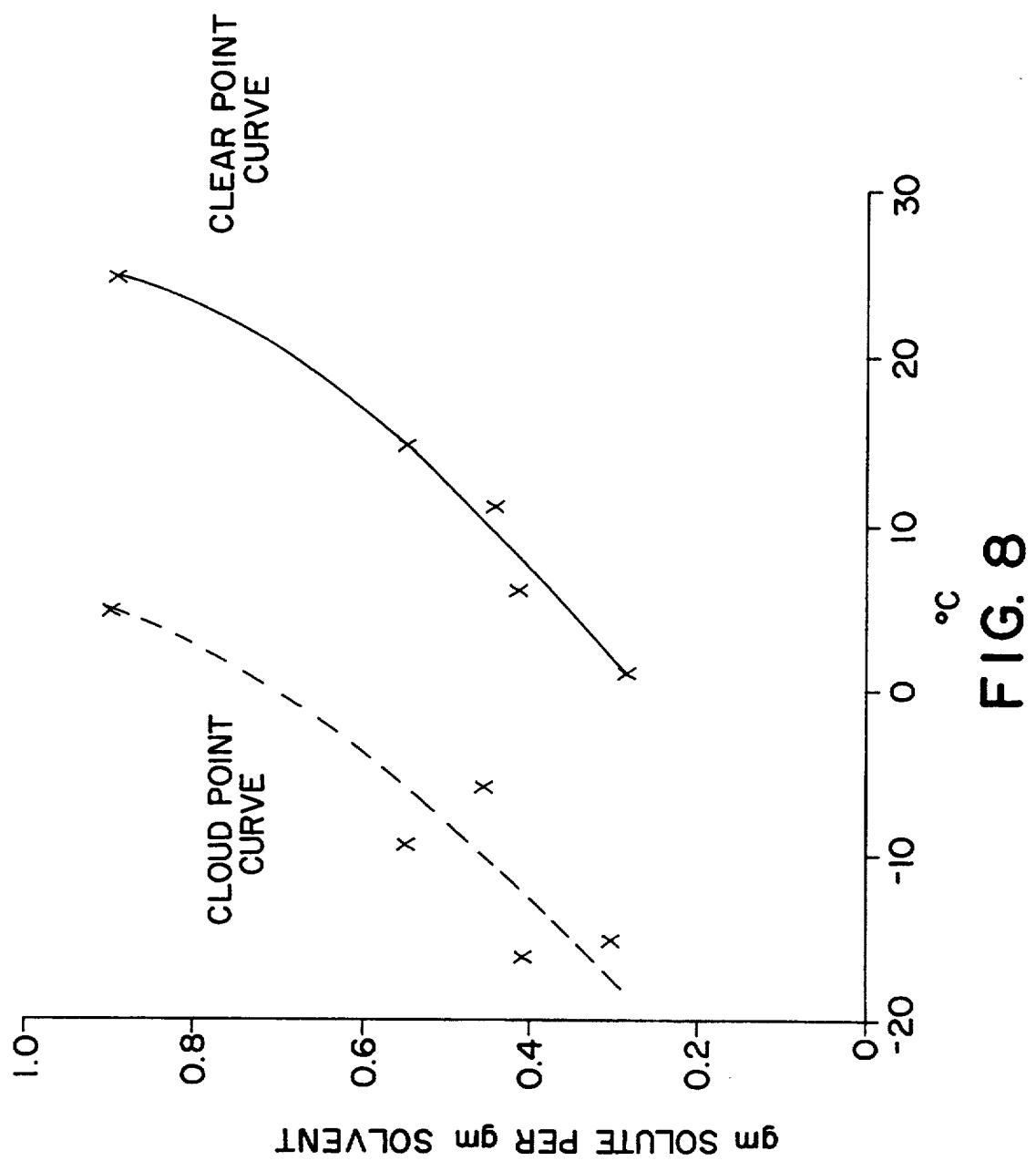
FIG. 8 is a solubility diagram for R- and S-2-(6-methoxy-2-naphthyl)propionaldehyde in acetone.

FIG. 8 summarizes solubility data for solids in acetone solvent. The data were obtained by visually obtaining a "cloud" point for a solution of known composition by slowly cooling the solution. After obtaining a "cloud" point the solution was slowly heated until a "clear" point was observed. The "clear" point represents the saturation temperature of the solution and the "cloud" point the temperature at which massive spontaneous nucleation occurs. The data are shown in Table 2.

Naproxen aldehydes [i.e., R— and S—2-(6-methoxy-2-naphthyl)propionaldehyde] are very soluble in acetone. The solubility of these aldehydes is very sensitive to temperature and a high degree of solution subcooling is required to nucleate the solution.

TABLE 2

Naproxen Aldehyde Solubility Data in Acetone

| Solids (wt %) | Ratio Solids/Liquid | Clear Point, ° C. | Cloud Point, ° C. |
|---|---|---|---|
| 29.0 | 0.41 | 6 | −17 |
| 35.3 | 0.55 | 15 | −9 |
| 30.0 | 0.43 | 11 | −6 |
| 22.0 | 0.28 | 1 | −15 |
| 47.0 | 0.89 | 25 | 5 |

C. Naproxen Aldehyde Distribution Coefficients

Figure 9A:
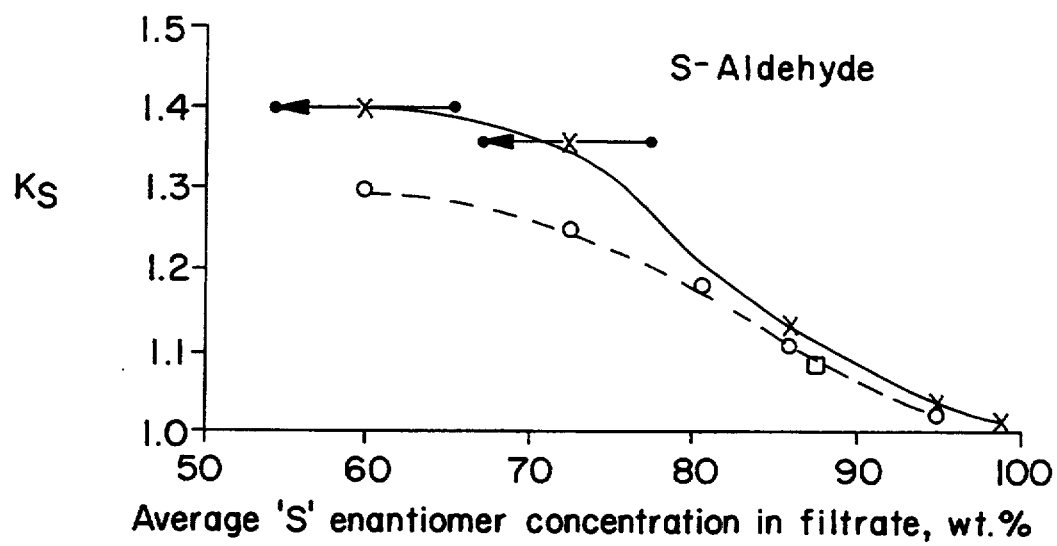
FIGS. 9 and 10 summarize distribution coefficients for R- and S-2-(6-methoxy-2-naphthyl)propionaldehyde in acetone.
Figure 9B:
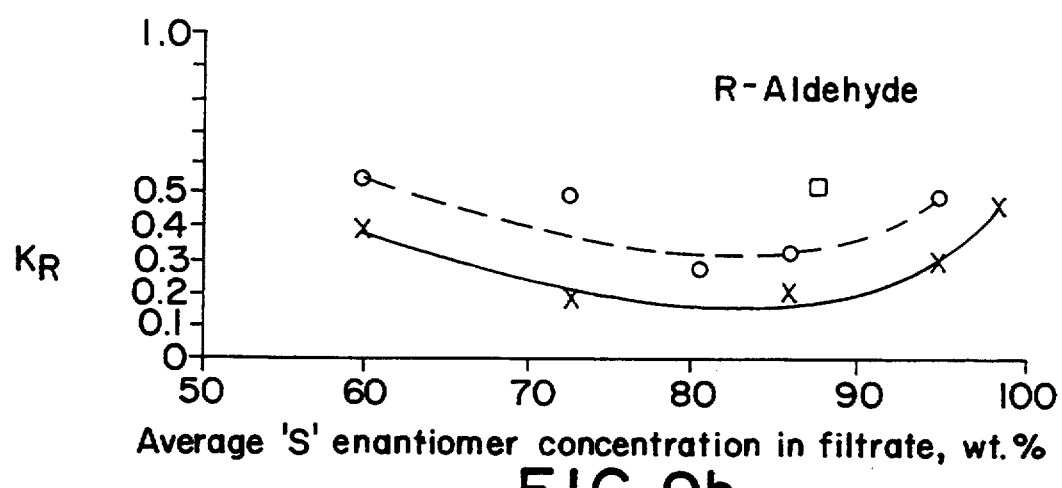
Figure 9C:
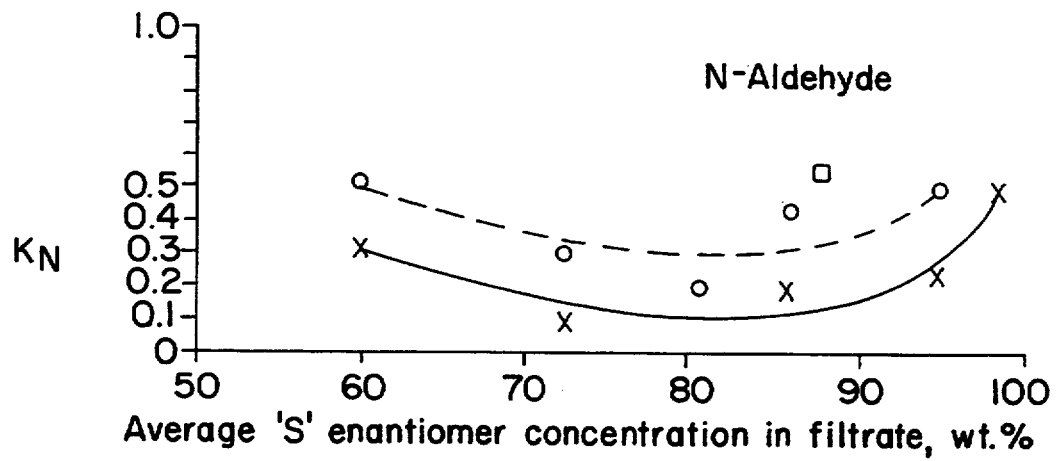
Figure 10A:
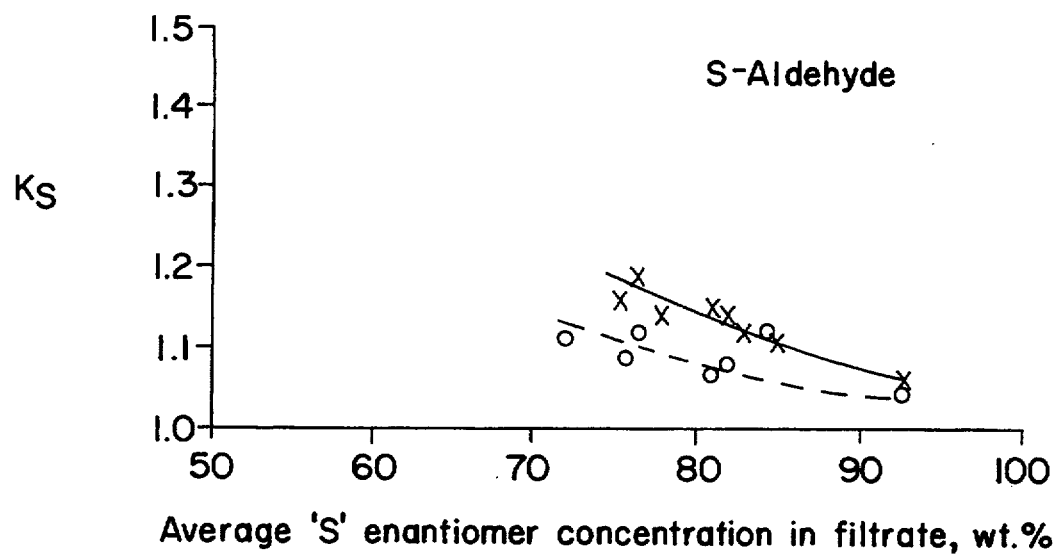
Figure 10B:
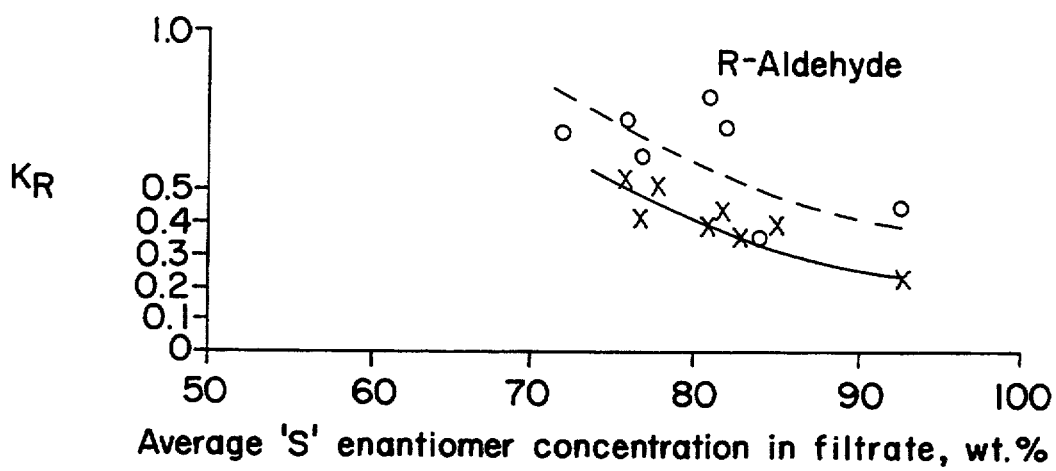
Figure 10C:
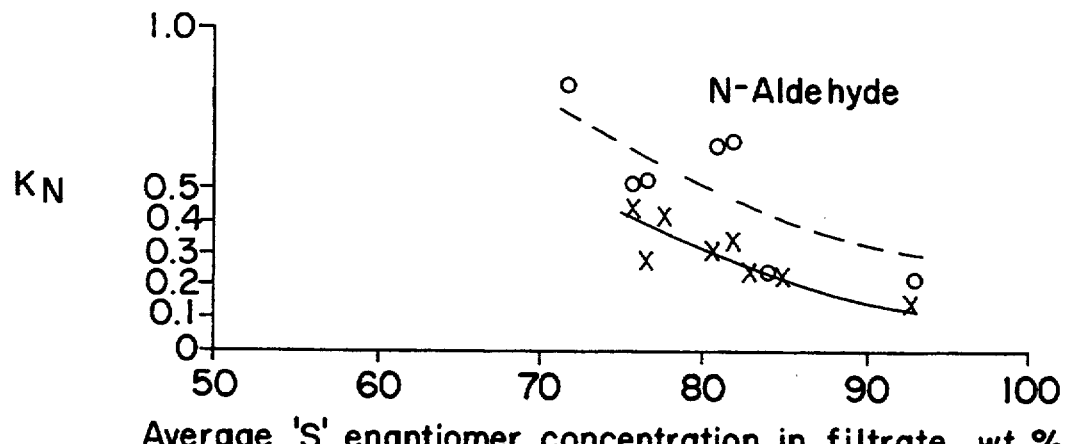

FIGS. 9 and 10 summarize distribution coefficients or "K" factors for "Naproxen aldehydes" [i.e., R— and S—2-(6-methoxy-2-naphthyl)propionaldehyde] crystallized from acetone solutions. The data are obtained from a variety of experimental runs over a wide range of liquid compositions.

$$K_A = \frac{C_A{}^S}{C_A{}^L}$$

wherein:
$C_A{}^S$ = aldehyde concentration in solid
$C_A{}^L$ = aldehyde concentration in liquid If K is greater than 1, then the crystallized solids are enhanced in that component. If K is less than 1 then the crystallized solids are depleted of the particular component.

Experimental data shown that the distribution coefficient for S-aldehyde, ($K_S$), is greater than 1 for the solution concentration range tested. Experimental evidence shows that S-aldehyde is enhanced by crystallization from acetone solutions ranging from 54 to 98.6% S isomer (i.e., S-2-6-methoxy-2-naphthyl)propionaldehyde). Also there is experimental evidence that verifies that R and N isomers are preferentially excluded via crystallization in the S solution range between 54 and 98.6%.

There is some evidence that the S and R isomers form a solid solution in the high purity S isomer range. Although the $K_S$ factor is greater than one, the stage efficiency is only 50% at the high purity end versus 80% or better in the middle range.

In the low S isomer region, the 54% S isomer residue liquid solidified after concentrating and cooling. It may be possible to squeeze a little more S isomer out of solution but 50% S is probably a lower limit on residue concentration via crystallization technology.

FIG. 9 also includes data from a single falling film crystallizer experiment conducted in the crystallizer shown in FIG. 6. Sufficient data were generated to show that the falling film crystallization was effective in upgrading the ee of the desired aldehyde. Distribution coefficients for falling film crystallization using the crystallizer of FIG. 6 are similar in magnitude to results obtained using the crystallizer of FIG. 5.

EXAMPLE 8

Recovery of S-Naproxen Aldehyde from Acetone Solution

A crude reaction product of an asymmetric hydroformylation reaction was produced with low ee (62%) to experimentally investigate the quality of "S-Naproxen aldehyde" [i.e., S-2-(6-methoxy-2-naphthyl)propionaldehyde] that can be recovered from solutions with high concentrations of corresponding isomeric R and N aldehydes. Using the cooling crystallization procedure described in Example 3 above (i.e., the solution is cooled to −15° C., reheated to 0° C. and this technique repeated three times before a final cool down to minus 15), a feed solution containing 77.6% S, 18.2% R and 4.2% N isomers and having an enantiomeric excess (ee) of 62% was processed. The resulting crystals were recovered on a vacuum filter and washed with cold acetone. The composition of the crystals was 95.5% S, 4.0% R, and 0.5% N isomers giving an enantiomeric excess of 92%. The filtrate recovered from the crystallization procedure described above in this Example and having a solids concentration of 65.5% S, 26.8% R and 7.7% N isomers was concentrated to 53% solids by evaporating acetone under vacuum. The concentrate so obtained was crystallized using the crystallization procedure described above in this Example. The composition of the crystalline solids obtained by the latter crystallization was 92.3% S, 7.0% R and 0.7% N isomers. The enantiomeric excess of those solids was 85.9%. The composition of the solids in the final filtrate was 54.1% S, 37.6% R and 8.3% N isomers.

EXAMPLE 9

Improving Enantiomeric Purity of 2-(p-Isobutylphenyl)propionaldehyde Through Melt Crystallization A solution was prepared consisting of p-isobutylstyrene (100.2 g), Iso(BHA-P)2-2R,4R-pentanediol (0.85 g), and Rh$_4$(CO)$_{12}$ (0.091 g). One hundred mL of the mixture so formed was charged to a 300 mL reactor which was pressurized with 1:1 H$_2$/CO. The mixture was stirred at 25° C. for 46 hours at 130 psi to effect hydroformylation. The crude reaction product was removed from the reactor and an aliquot removed to determine the composition of the product.

GC analysis on a beta-cyclodextrin chiral capillary column (Cyclodex-B TM) indicated that 99.4% of the olefin starting material had been converted to aldehydes and that a 42:1 ratio of 2-(p-isobutylphenyl)propionaldehyde to 3-(p-isobutylphenyl)propionaldehyde had been obtained. Oxidation of the aldehyde products followed by chiral gas chromatography of the resulting carboxylic acids indicated that an 85±5% ee of the desired S-aldehyde [i.e., S-2-(p-isobutylphenyl)propionaldehyde] was produced.

A portion (25 mL, 23.54 g) of the crude product was flash distilled to separate the products from the catalyst. The first cut (12.4 g) was obtained at 89°–92° C. head temperature at a pressure of 1 mm of Hg. A second cut (9.4 g) was obtained at 83°–4° C. at 0.6 mm of rig, and a small amount was left as residue. The second cut was partially frozen and some liquid (3.27 g) was withdrawn, first with a pipet and then a fritted glass filter stick with the liquid at −12° to −17° C.

Oxidation of portions of the liquid and crystals with sodium chlorite followed by chiral gas chromatography of the resulting carboxylic acids indicated 92+1 and 75+2% ee for the S-aldehyde in the crystals and and liquid respectively. The ratios of the concentrations of other impurities in liquid to their concentrations in the crystals averaged 2.2 and the b/n ratio in the crystals was 54:1.

The oxidation with sodium chlorite referred to above was conducted as follows:

A mixture of 0.28 gram of aldehyde and 2.0 mL of distilled water was cooled to 0° C. and stirred. Aqueous sodium sulfamate (3 mL of 1M, adjusted to pH 5 with phosphoric acid) and sodium chlorite (0.61 mL of 20%) solutions were added. After 15 minutes, the cooling bath was removed and the solution was stirred for an additional 15 minutes as it was allowed to warm to room temperature. The pH was adjusted to 9.5 with 0.5 mL of 1N sodium hydroxide and the material rinsed with water into a separatory funnel. The solution was shaken with added dichloromethane (10 mL) to extract neutral compounds. The aqueous layer was separated and acidified to pH<2 with concentrated hydrochloric acid. The cloudy mixture that formed was extracted with 20 mL of dichloromethane, toluene was added as an internal standard, and a small sample was taken to determine the yields of branched and normal acids by gas chromatography. The remaining solution was dried over anhydrous magnesium sulfate and filtered. The dichloromethane was removed with a rotary evaporator under vacuum (~150 mm Hg) with the bath at 60° C. The residue (0.02 g) was dissolved in toluene and analyzed by chiral gas chromatography.

What is claimed is:

1. A process for producing an optically active aldehyde (first aldehyde) containing a reduced amount of the corresponding enantiomeric aldehyde (second aldehyde) which process comprises: (1) providing an initial solution containing a non-eutectic mixture of the first aldehyde and the second aldehyde, which mixture has a composition in the compositional region where only the first aldehyde crystallizes when its solubility limit in the solution is exceeded, and (2) maintaining the solution at a temperature above the eutectic temperature of the mixture and under conditions such that the solubility limit of the first aldehyde is exceeded so as to form a crystalline first aldehyde containing relatively less of the second aldehyde than was present in the initial solution.

2. A process as claimed in claim 1 wherein the first aldehyde is S-2-(6-methoxy-2-propionaldehyde and the second aldehyde is R-2-(6-methoxynaphthyl)-propionaldehyde.

3. A process as claimed in claim 1 wherein the first aldehyde is S-2-(p-isobutylphenyl)propionaldehyde and the second aldehyde is R-2-(p-isobutylphenyl)propionaldehyde.

4. A process as claimed in claim 1 wherein step (2) involves cooling the initial solution in a falling film crystallizer to achieve crystallization of the first aldehyde on a surface of the crystallizer.

5. A process as claimed in claim 4 in which the first aldehyde crystallizes on a surface of the crystallizer and is dissolved by a solvent at a temperature below the melting point of the first aldehyde to avoid substantial racemization of the first aldehyde.

6. A process as claimed in claim 1 wherein step (2) is conducted by cooling the initial solution in stages wherein (a) the solution (depleted solution) resulting from crystallization in a first stage is separated from the crystals formed in the first stage, (b) the depleted solution so formed is cooled in a second stage to form additional crystals and (c) additional stages are conducted per (a) and (b) until the desired degree of crystallization is achieved.

7. The process of claim 1 in which the optically active product has an enantiomeric excess of greater than 96%.

8. The process of claim 1 wherein the regio-selectivity of the product, in terms of its branch to normal isomer ratio, is greater than 1000:1.

9. A process as claimed in claim 1 wherein step (1) comprises contacting a prochiral or chiral compound in the presence of an optically active metal-ligand complex catalyst to produce an optically active aldehyde mixture, said optically active metal-ligand complex catalyst comprising a metal complexed with an optically active ligand having the formula:

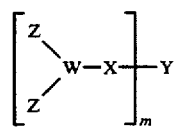

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active.

10. The process of claim 9 which comprises isomerization, aldol condensation or hydroformylation.

11. A process as claimed in claim Q wherein step (1) comprises a hydroformylation process which comprises contacting a prochiral or chiral olefinically unsaturated organic compound with carbon monoxide and hydrogen in the presence of an optically active rhodium-ligand complex catalyst to produce an optically active product, said optically active metal-ligand complex catalyst comprising a metal complexed with an optically active ligand having the formula

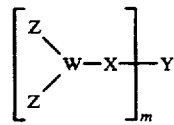

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active; with the provisos that when each W is phosphorus and each X is a covalent bond, then the Z substituents cannot all be hydrocarbon residues having a carbon atom directly bonded to phosphorus, and when Y is a substituted 2 carbon aliphatic chain and m is a value of 2 and both W substituents are phosphorus and one X substituent is oxygen and the other X substituent is nitrogen, then the Z substituents cannot all be phenyl, and when Y is a substituted tetrahydropyran and m is a value of 2 and both W substituents are phosphorus and the X substituents are both oxygen, then the Z substituents cannot all be aryl.

12. A process as claimed in claim 11 wherein the ligand is (2R,4R)-Di[2,2'-(3,3'-di-tert-butyl-5,5'-dimethoxy-1,1'-biphenyl)]2,4-pentyl diphosphite.

13. The process of claim 11 in which the optically active metal-ligand complex catalyst comprises a metal selected from a Group VIII, Group IB and Group VIB metal complexed with an optically active ligand having the formula selected from

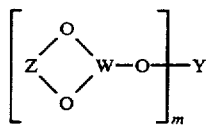

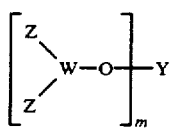

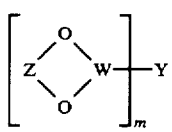

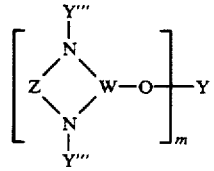

wherein W, Y, Z and m are as defined in claim 1 and Y''' is the same or different and is hydrogen or a substituted or unsubstituted hydrocarbon residue.

14. The process of claim 11 in which the olefinically unsaturated organic compound is p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether or vinyl chloride.

15. The process of claim 11 in which the product of the hydroformylation contains, as the first aldehyde, S-2-(p-isobutylphenyl)propionaldehyde, S-2-(6-methoxy-2-naphthyl)propionaldehyde S-2-(3-benzoylphenyl)propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]-propionaldehyde, S-2-(2-methylacetaldehyde)-5-benzoylthiophene, S-2-(3-phenoxy)propionaldehyde, S-2-phenylbutyraldehyde, S-2-(4-isobutylphenyl)-butyraldehyde, S-2-phenoxypropionaldehyde, S-2-chloropropionaldehyde, R-2-(3-benzoylphenyl)-propionaldehyde or R-2-(3-fluoro-4-phenyl)-phenylpropionaldehyde.

* * * * *

UNITED STATES PATENT AND TRADEMARK OFFICE
CERTIFICATE OF CORRECTION

PATENT NO. : 5,430,194
DATED : July 4, 1995
INVENTOR(S) : Bruce A. Barner et al.

It is certified that error appears in the above-identified patent and that said Letters Patent is hereby corrected as shown below:

Col.41, Claim 2, line 2, "S-2-(6-methoxy-2-propionaldehyde" should read
-- S-2-(6-methoxy-2-naphthyl)propionaldehyde --.

Col.41, Claim 2, line 3, "R-2-(6-methoxynaphthyl)-propionaldehyde" should read
-- R-2-(6-methoxy-2-naphthyl)propionaldehyde --.

Col.42, Claim 11, line 1, "Q" should read -- 9 --.

Signed and Sealed this

Nineteenth Day of March, 1996

Attest:

BRUCE LEHMAN

*Attesting Officer*  *Commissioner of Patents and Trademarks*